(12) United States Patent
Bischoff et al.

(10) Patent No.: US 6,291,423 B1
(45) Date of Patent: Sep. 18, 2001

(54) LIPID COMPLEXES FOR TRANSFERRING AT LEAST A THERAPEUTICALLY ACTIVE SUBSTANCE, IN PARTICULAR A POLYNUCLEOTIDE INTO A TARGET CELL AND USE IN GENE THERAPY

(75) Inventors: Rainer Bischoff, Barsebäck (SE); Danis Heissler, Eckbolsheim; Abdesslame Nazih, Strasbourg, both of (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/242,258

(22) PCT Filed: Jun. 11, 1998

(86) PCT No.: PCT/FR98/01220
§ 371 Date: Feb. 12, 1999
§ 102(e) Date: Feb. 12, 1999

(87) PCT Pub. No.: WO98/56423
PCT Pub. Date: Dec. 17, 1998

(30) Foreign Application Priority Data

Jun. 12, 1997 (FR) .................................................. 97 07290

(51) Int. Cl.$^7$ ...................... A61K 31/4965; A61K 47/48; A61K 38/00; A61K 48/00; C07D 295/15
(52) U.S. Cl. ........................... 514/2; 514/44; 514/252.12; 544/400; 424/450; 435/455; 435/458; 530/403; 530/405
(58) Field of Search .............................. 424/450; 435/458; 435/455; 514/44, 2; 544/400; 530/403, 405; 536/23.1

(56) References Cited

U.S. PATENT DOCUMENTS 5,635,487 * 6/1997 Wolff et al. ............................. 514/44
5,744,335 * 4/1998 Wolff et al. ....................... 435/172.3

FOREIGN PATENT DOCUMENTS

WO 95/14651 * 6/1995 (WO) .
95 14651 6/1995 (WO) .

OTHER PUBLICATIONS

Anderson, "Human gene therapy", Nature, 392(Supp.):25–30, Apr. 1998.*
Verma et al., "Gene therapy–promises, problems and prospects", Nature, 389;239–242, Sep. 1997.*
Zabner, "Cationic lipids used in gene transfer", Adv. Drug Deliv. Rev., 27:17–28, 1997.*

J.A. Riggs et al, "Nucleotide carrier mixture with transport selectivity for Riboncleoside–5'–phosphates", Tetrahedron Letters, vol. 37, No. 35, 1996, pp. 6303–6306, XP002079553 Oxford GB.

Solodin, Igor et al, "Synthesis of amphiphilic piperidinium derivatives. Cationic lipids. Part 4" Synlett (1996), (7), 619 Cohen: Synles; ISSN: 0936–5214, XP002056223.

* cited by examiner

Primary Examiner—Scott D. Priebe
Assistant Examiner—Peter Brunovskis
(74) Attorney, Agent, or Firm—Burns, Doane, Swecker & Mathis, L.L.P.

(57) ABSTRACT

The invention concerns a complex comprising at least a lipid and at least a therapeutically active substance useful for transferring said substance into a target cell, characterised in that said lipid is of formula (I): in which: $n_1$, $n_2$, identical or different are whole numbers between 0 and 1; $R_1$, $R_2$, identical or different are: a) selected among the group consisting of a hydrogen atom and alkyl radicals with 1 to 6 carbon atoms optionally substituted, independently of one another, by a hydroxyl radical; or b) in one particular case for which $n_1=n_2=1$, $R_1$ and $R_2$ can form together a divalent alkylene chain of 2 to 3 carbon atoms ($C_2$–$C_3$); $R_3$, $R_4$, identical or different are alkyl radicals of 1 to 6 carbon atoms or can together form a divalent alkylene chain of 2 to 3 carbon atoms ($C_2$–$C_3$); m, p, identical or different are whole numbers between 1 and 10; $R_5$, $R_6$, identical or different are selected in the group consisting of radicals of formula: 1) $R_7$ C(=O)—X— in which: X=NH, O, S; $R_7$ is an alkyl or alkenyl radical of 6 to 23 carbon atoms ($C_6$–$C_{23}$), linear or branched; 2) $R_8R_9NC(=O)$— in which: $R_8$, $R_9$, identical or different are selected among the group consisting of the hydrogen atom or alkyl or alkenyl radicals of 6 to 23 carbon atoms, linear or branched, provided that $R_8$, $R_9$, cannot simultaneously correspond to the hydrogen atom; 3) and one of the radicals $R_5$, $R_6$ can moreover correspond to the hydrogen atom. The invention also concerns the use of said complex in gene therapy.

7 Claims, 14 Drawing Sheets

LIPID COMPLEXES FOR TRANSFERRING AT LEAST A THERAPEUTICALLY ACTIVE SUBSTANCE, IN PARTICULAR A POLYNUCLEOTIDE INTO A TARGET CELL AND USE IN GENE THERAPY

The present invention relates to novel complexes comprising at least one lipid compound as defined below and at least one therapeutically active substance. More particularly, the present invention relates to the use of said complexes for transferring at least one therapeutically active substance containing negative charges, in particular a polynucleotide, into a target cell, particularly a vertebrate cell, and more particularly a mammalian cell.

Gene transfer into a given cell is the very basis of gene therapy. This technology, whose field of application is vast, makes it possible to envisage treating serious diseases for which the standard alternative therapies are ineffective, or even nonexistent, and relates equally to diseases of genetic origin (hemophilia, mucoviscidosis, myopathy, etc.) and acquired diseases (cancer, AIDS, etc.).

In the course of the last 30 years, many tools have been developed for introducing various heterologous genes into cells, in particular mammalian cells. These various techniques can be divided into two categories. The first category relates to physical techniques such as microinjection, electroporation or particle bombardment, which, although effective, are largely limited to in vitro applications and are cumbersome and difficult to carry out. The second category involves techniques relating to molecular biology and cell biology, for which the gene to be transferred is combined with a vector of biological or synthetic nature which promotes the introduction of said material.

The vectors which are currently the most effective are viral vectors, in particular adenoviral or retroviral vectors. The techniques developed are based on the natural properties which these viruses have for crossing cell membranes, avoiding the degradation of their genetic material and enabling their genome to penetrate into the nucleus. These viruses have already been the subject of many studies and some of them are already used experimentally as gene vectors in man for the purpose, for example, of a vaccination, an immunotherapy or a therapy aimed at compensating for a genetic deficiency. However, this viral approach has many limitations, in particular on account of the restricted cloning capacity in the viral genome, risks of dissemination of the infectious viral particles produced into the host body and into the environment, risk of artefactual mutagenesis by insertion into the host cell in the case of retroviral vectors, and strong induction of immune and inflammatory responses in vivo during therapeutic treatment, which considerably limits the number of administrations which can be envisaged (Mc Coy et al, 1995, Human Gene Therapy, 6, 1553–1560; Yang et al., 1996, Immunity, 1, 433–442). These many drawbacks, in particular in the context of a use in man, have led several teams to develop alternative systems for transferring polynucleotides.

Several non-viral methods are available at the present time. Mention is made, for example, of the coprecipitation with calcium phosphate, the use of receptors which mimic viral systems (for a revue see Cotten and Wagner, 1993, Current Opinion in Biotechnology, 4, 705–710), or the use of polymers such as polyamidoamine (Haensler and Szoka, 1993, Bioconjugate Chem., 4, 372–379), or of a polymer such as those given in WO 95/24221 which describes the use of dendritic polymers, document WO 96/02655 which describes the use of polyethyleneimine or of polypropyleneimine and documents U.S. Pat. No. 5,595,897 and FR 2,719,316 which describe the use of polylysine conjugates. Other non-viral techniques are based on the use of liposomes whose value as agents for introducing into cells pharmaceutically active substances such as, for example, DNA, RNA or proteins has been widely described in the literature. To this end, several teams have already proposed the use of cationic lipids which have a strong affinity for cell membranes and/or nucleic acids. The reason for this is that, although it has been shown, in the case of nucleic acids, that this type of macromolecule is capable of crossing the plasma membrane of certain cells in vivo (WO 90/11092), the fact nevertheless remains that the efficacy of the transfection observed is still very limited, in particular on account of the polyanionic nature of nucleic acids which prevents them from crossing the cell membrane, which itself has a net negative apparent charge. Since 1989 (Felgner et al., Nature, 337, 387–388) cationic lipids have been presented as advantageous molecules for promoting the introduction of large anionic molecules, such as nucleic acids, into certain cells. These cationic lipids are capable of complexing with anionic molecules, thus tending to neutralize the negative charges on said molecules and to promote their approach toward cell walls. Many teams have already developed various cationic lipids. As examples, mention may be made of DOTMA (Felgner et al., 1987, PNAS, 84, 7413–7417), DOGS or Transfectam™ (Behr et al., 1989, PNAS, 86, 6982–6986), DMRIE and DORIE (Felgner et al., 1993, Methods 5, 67–75), DC-CHOL (Gao and Huang, 1991, BBRC, 179, 280–285), DOTAP (McLachlan et al., 1995, Gene Therapy, 2, 674–622) or Lipofectamine™, as well as those described in patent applications WO 91/16024 or WO 95/14651 or WO-A-94/05624.

More particularly, patent application WO-A-95/14651 describes cationic lipids of formula:

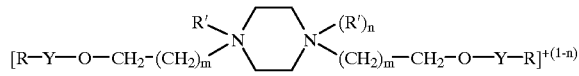

in which R is a linear chain, an aliphatic alkyl group of 5 to 29 carbon atoms, Y is —$CH_2$— or CO, R' is a lower alkyl radical, m is an integer from 0 to 7, n is 0 or 1, the total number of carbon atoms in R and $(CH_2)_m$ being at least equal to 10.

However, several studies (as examples, see Mahato et al., J. Pharm. Sci., 1995, 84, 1267–1271, Thierry et al., 1995, P.N.A.S, 92, 9742–9746) have demonstrated that the efficacy of the transfer into cells of the anionic macromolecule can vary as a function in particular of the interaction between the complexes and the cell membranes, the cell considered, the lipid composition of the cationic compounds, the size of the complexes formed with the anionic molecules and, more particularly, the ratio of positive and negative charges on the different components of said complex. The mechanisms which in particular allow the interaction of the complexes with cell membranes and the transfer of the complexes into the cell are still largely unknown and researchers are proceeding in their studies with a highly empirical approach. Other factors such as, for example, the formation of complexes, the stability, the behavior in vivo, or optionally their toxicity, also make the choice of lipids not obvious in principle. It is consequently desirable to propose other cationic lipids, which make it possible to design novel non-viral vectors or lipid complexes optionally having properties that are better than or different from those already described.

The present invention relates, firstly, to a complex comprising at least one lipid and at least one therapeutically active substance, in particular containing negative charges, which can be used for transferring said substance into a target cell, characterized in that said lipid is of formula I:

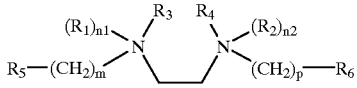

I in which:

$n_1$ and $n_2$, which may be identical or different, are integers chosen from 0 and 1, $R_1$ and $R_2$, which may be identical or different, are:

a) chosen from the group consisting of a hydrogen atom and alkyl radicals of 1 to 6 carbon atoms which are optionally substituted, independently of each other, with a hydroxyl radical, or b) according to a specific case for which n1=n2=1, R1 and R2 can together form a divalent alkylene chain of 2 to 3 carbon atoms (C2–C3), $R_3$ and $R_4$, which maybe identical or different, are alkyl radicals of 1 to 6 carbon atoms or can together form a divalent alkylene chain of 2 to 3 carbon atoms (C2–C3), m and p, which may be identical or different, are integers between 1 and 10, $R_5$ and $R_6$, which may be identical or different, are chosen from the group consisting of the radicals of formula:

1) $R_7$ C(=O)—X— in which:

X=NH, O or S, $R_7$ is a linear or branched, alkyl or alkenyl radical of 6 to 23 carbon atoms ($C_6$–$C_{23}$)

2) $R_8R_9NC(=O)$— in which:

$R_8$ and $R_9$, which may be identical or different, are chosen from the group consisting of a hydrogen atom or linear or branched, alkyl or alkenyl radicals of 6 to 23 carbon atoms, on condition that $R_8$ and $R_9$ cannot simultaneously correspond to a hydrogen atom, and 3) it also being possible for one of the radicals $R_5$ and $R_6$ to correspond to a hydrogen atom.

According to a very specific case, when $n_1$ or $n_2$ is equal to 0 and $n_2$ or $n_1$ is equal to 1, respectively, it is possible to form an alkylene chain containing only one carbon atom between the two nitrogens with RI and R2. Such a chain can also be obtained between the two nitrogens with R3 or R4.

The term "alkenyl" is intended to indicate that the carbon chain in question can comprise one or more double bond(s) along said chain.

According to a variant, the lipid included in a complex of the invention is a lipid of formula II:

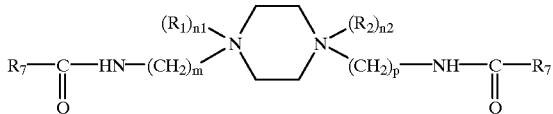

II in which:

$n_1$ and $n_2$, which may be identical or different, are chosen from the integers 0 and 1, $R_1$ and $R_2$ which may be identical or different, are chosen from the group consisting of a hydrogen atom and alkyl radicals of 1 to 6 carbon atoms, optionally substituted, independently of each other, with hydroxyl radicals, in the specific case in which $n_1=n_2=1$, $R_1$ and $R_2$ can together form a divalent alkylene chain of 2 to 3 carbon atoms, m and p, which may be identical or different, are integers between 1 and 10, $R_7$, which may be identical or different, is a linear or branched, alkyl or alkenyl radical of 6 to 23 carbon atoms.

Preferably, the radicals $R_7$ C(=O), which may be identical or different, are radicals of 13 to 18 carbon atoms, in particular oleoyl, stearoyl, palmitoyl and myristoyl radicals.

According to an advantageous case of the invention, said lipid is in cationic form, i.e. it is in protonated form by binding a proton to one or more nitrogen atoms. In this case, said cationic lipid is associated with one or more biologically acceptable anions such as, for example, the trifluoroacetate, halogen, monomethylsulfate, acetate or phosphate, iodide, chloride, bromide, etc. anion. Needless to say, and in general, when the sum $n_1+n_2$ is 1 or 2, said lipid is associated with an anion of negative charge equal to $n_1+n_2$ or to two anions of total charge equal to $n_1+n_2$, which are biologically acceptable. The expression "biologically acceptable anion" means that the anions are such that the cationic lipids can be introduced into the cell or can be present in the cell membrane.

Preferably, the lipids included in the complexes according to the invention are chosen from the group consisting of the compounds of the following formulae, optionally in cationic form:

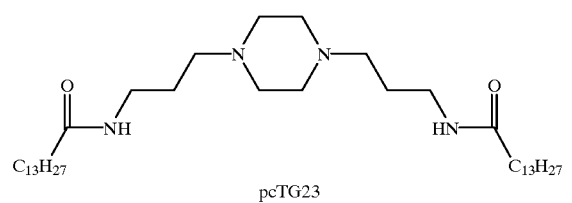

III pcTG23

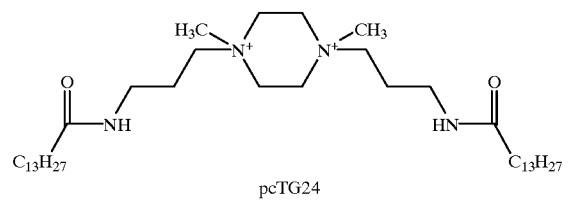

IV pcTG24

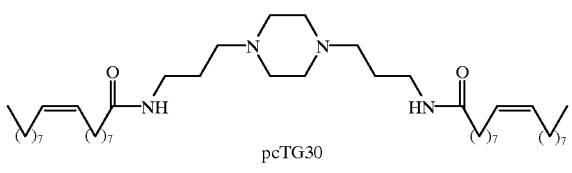

V pcTG30

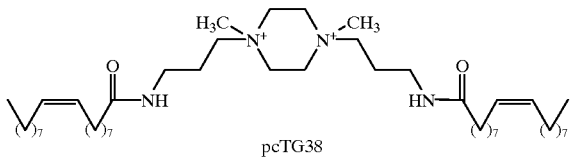

VI pcTG38

The cationic lipids of formula II used according to the invention a re prepared by reacting a tetramine of formula:

XVIII with acids of formula R₇COOH,

R₇, m and p having the same meaning as in the compound of formula II, to give the corresponding diamide.

This latter compound is optionally alkylated on the nitrogen atoms of the ring, by reaction with an alkyl halide. It can also be protonated on the same nitrogen atoms by treatment with an acid.

The alkylation reaction is carried out using an alkyl halide or alkylene dihalide in organic medium.

For a practical implementation, reference will be made to the preparation examples given in the description.

The processes described are generally applicable to the syntheses of lipids used according to the invention, optionally after adaptations which are within the capabilities of those skilled in the art.

According to another variant, the lipid included in the complexes of the invention corresponds to the formula VII:

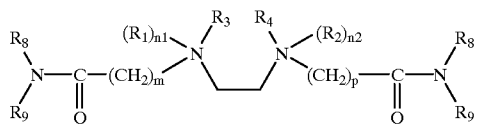

VII in which:

$n_1$ and $n_2$, which may be identical or different, are integers chosen from 0 and 1, $R_1$ and $R_2$, which may be identical or different, are:

a) chosen from the group consisting of a hydrogen atom and alkyl radicals of 1 to 6 carbon atoms which are optionally substituted, independently of each other, with a hydroxyl radical, or b) according to a specific case for which $n_1=n_2=1$, $R_1$ and $R_2$ can together form a divalent alkylene chain of 2 to 3 carbon atoms (C2–C3), $R_3$ and $R_4$, which may be identical or different, are alkyl radicals of 1 to 6 carbon atoms or can together form a divalent alkylene chain of 2 to 3 carbon atoms (C2–C3), m and p, which may be identical or different, are integers between 1 and 10, $R_8$ and $R_9$, which may be identical or different, are chosen from the group consisting of a hydrogen atom or linear or branched, alkyl or alkenyl radicals of 6 to 23 carbon atoms, on condition that $R_8$ and $R_9$ cannot simultaneously correspond to a hydrogen atom, and the radicals $NR_8R_9$ on each side of the molecule can be different.

Preferably, $R_8$ and $R_9$ are chosen from alkyl or alkenyl radicals of 6 to 23 carbon atoms.

Preferably, the lipids in the complexes are chosen from the group consisting of the compounds of the following formulae:

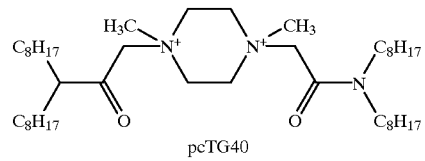

pcTG40

VIII

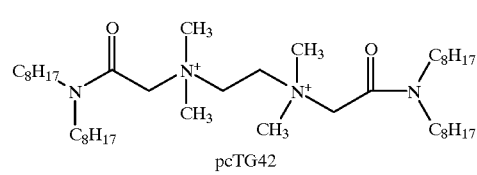

pcTG42

IX

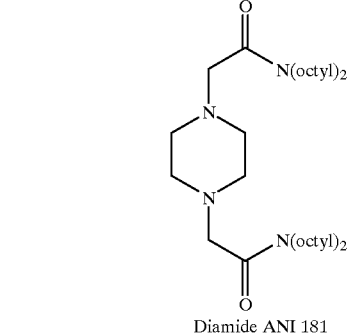

Diamide ANI 181

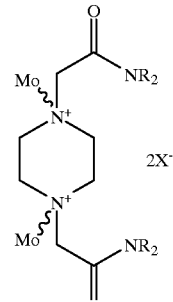

ANII 16 F1, ANII 16 F2:R = —(CH₂)₇Me, X = I⁻
ANII 150 F1, ANII 150 F2:R = —(CH₂)₁₃Me, X = Br⁻
ANII 157 F1, ANII 157 F2:R = oleyl, X = Br

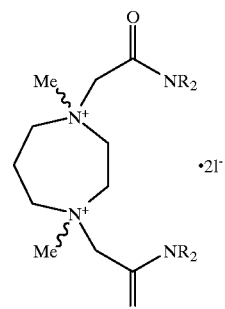

ANII 22 F1, ANII 22 F2:R = —(CH₂)₇Me
ANII 152 F1, ANII 152 F2:R = —(CH₂)₁₃Me

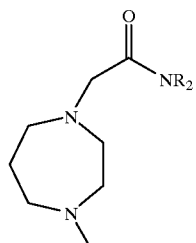

Diamide ANII 21 R = ——(CH$_2$)$_7$Me
Diamide ANII 151 R = ——(CH$_2$)$_{13}$Me

According to another variant, the lipid used corresponds to the formula

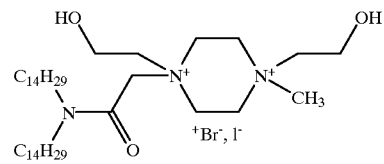

in which:

$n_1$ and $n_2$, which may be identical or different, are integers chosen from 0 and 1, $R_1$ and $R_2$, which may be identical or different, are:

a) chosen from the group consisting of a hydrogen atom and alkyl radicals of 1 to 6 carbon atoms which are optionally substituted, independently of each other, with a hydroxyl radical, or b) according to a specific case for which $n_1=n_2=1$, $R_1$ and $R_2$ can together form a divalent alkylene chain of 2 to 3 carbon atoms (C2–C3), m and p, which may be identical or different, are integers between 1 and 10, $R_8$ and $R_9$, which may be identical or different, are chosen from the group consisting of a hydrogen atom or linear or branched, alkyl or alkenyl radicals of 6 to 23 carbon atoms, on condition that $R_8$ and $R_9$ cannot simultaneously correspond to a hydrogen atom.

Preferably, such lipids are chosen from the group consisting of the compounds of the following formulae:

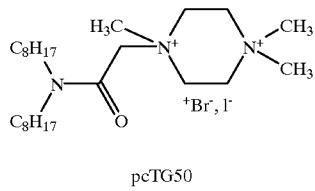

pcTG50

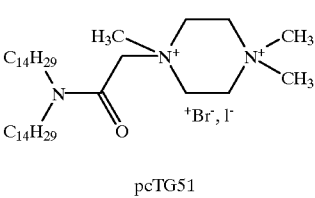

pcTG51

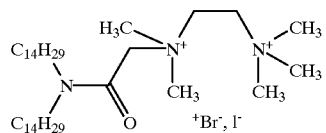

pcTG52

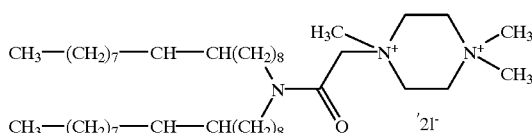

pcTG53

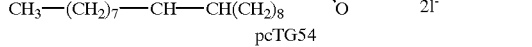

pcTG54

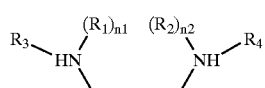

pcTG55

Such cationic lipids can be prepared by reacting a diamine of formula:

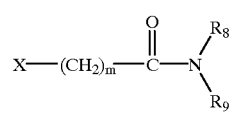

with an ω-halo amide of formula:

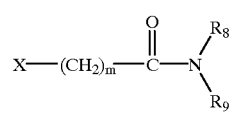

$R_1$, $R_2$, $R_3$, $R_4$, m, $R_8$ and $R_9$ having the same meaning as in formula VII. X is an atom of a halide XX.

One of the bromides used as halogen (m=1, p=1, $R_8=R_9$=octyl) is already described in Li, T.; Diederich, F. J. Org. Chem. 1992, 57, 3449–3454, as is its use in the dialkylation of N(CH$_2$—CH$_2$)$_3$N (=diazabicyclo[2.2.2] octene).

However, the lipids included in the complexes of the invention cannot be limited to those obtained by the preparation methods described above.

Moreover, according to preparation variants of the invention, the lipids included in the complexes and described above can have the following variations, which may or may not be taken in combination with each other:

preferably, $R_1$ and/or $R_2$ or $R_3$ and/or $R_4$ is a methyl radical;

preferably, $R_1$ and $R_2$ or $R_3$ and $R_4$ together form an ethylene chain;

preferably, $R_1$ and $R_2$ or $R_3$ and $R_4$ together form a propylene chain;

preferably, m and/or p are integers between 1 and 6;

in the case of formula X, preferably, m is an integer between 1 and 6 and p=1.

According to a specific case of the invention, one or more ligands of interest can be bound to the lipids via at least one of the nitrogen atoms, or even via one of the group R. Such ligands can consist in particular of a labeling molecule (see labeling molecules in U.S. Pat. No. 4,711,955), a cell targeting molecule (GRP peptide, gastrin releasing peptide, for example), or an anchoring molecule. Such elements can allow targeting toward one specific cell type and facilitate penetration into the cell, lysis of the endosomes or alternatively intracellular transport, and are widely described in the literature. They can be, for example, all or some sugars, peptides, oligonucleotides, lipids, hormones, vitamins, antigens, antibodies, specific membrane-receptor ligands, ligands capable of reacting with an anti-ligand, fusogenic peptides, nuclear localization peptides, or a combination of such compounds. Mention may be made more particularly of galactosyl residues for targeting the asialoglycoprotein receptor at the surface of liver cells, the fusogenic peptide INF-7 derived from the subunit HA-2 of influenza virus hemagglutinin (Plank et al. 1994, J. Biol. Chem. 269, 12918–12924) or a nuclear localization signal derived from the T antigen of the SV40 virus (Lanford and Butel, 1984, Cell 37, 801–813) or from the protein EBNA-1 of the Epstein-Barr virus (Ambinder et al., 1991, J. Virol. 65, 1466–1478). Such conjugates can be readily obtained according to the techniques widely described in the literature.

It should moreover be pointed out that the invention also relates to complexes comprising one, the other or a mixture of the diastereoisomers (cis and/or trans) corresponding to the lipid included in such a complex. The reason for this is that the Applicant has moreover shown that one or other of these isomers (cis or trans) can have better properties than its opposite isomers (trans or cis, respectively) in terms of transfection efficacy. The identification of the isomers can readily be carried out according to techniques well known to those skilled in the art, in particular by measuring the NMR spectrum and/or crystallization of the composition containing the lipid analyzed.

As examples of diastereoisomers, mention may be made in particular of the lipids having the following formulae:

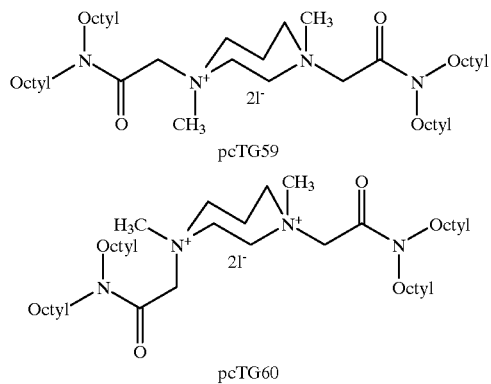

pcTG59 pcTG60

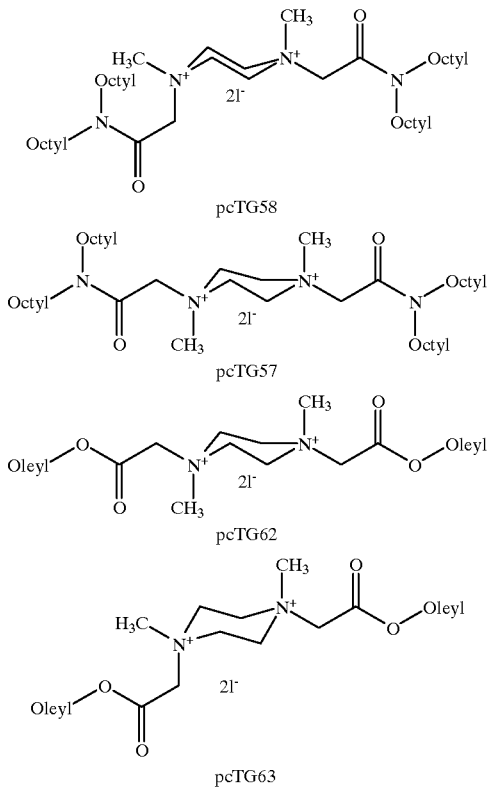

pcTG58 pcTG57 pcTG62 pcTG63

According to another aspect, the invention also relates to a lipid/therapeutically active substance complex as described above, characterized in that it also comprises at least one adjuvant capable of improving the formation of the complexes between a said lipid and a said therapeutically active substance, or of improving the functioning of these complexes toward the cell.

Preferably, such an adjuvant will be a neutral or zwitterionic lipid such as, for example, a triglyceride, a diglyceride, cholesterol (see, for example, U.S. Pat. No. 5,438,044), in particular, a neutral or zwitterionic lipid which is or is derived from a phosphatidylethanolamine (PE), phosphatidylcholine, phosphocholine, sphingomyelin, ceramide or cerebroside. Advantageously, dioleoylphosphatidylethanolamine (DOPE) or phosphatidylethanolamine (PE) will be chosen.

The weight ratio between the lipid and said adjuvant is generally between 0.1 and 10, it being understood that this ratio can vary depending on the nature of the components considered. A person skilled in the art has sufficient knowledge to allow these minor adaptations. It is also possible to use a mixture of neutral and/or zwitterionic lipids or alternatively a mixture of cationic lipids and of neutral and/or zwitterionic lipids.

According to another aspect, the invention also relates to a composition intended for transferring a therapeutically active substance into a target cell, comprising at least one lipid such as those described above for the complexes and at least one adjuvant as described above.

According to one specific embodiment, said therapeutically active substance in accordance with the invention is chosen from nucleic acids and proteins. Preferably, the active substance in the complex according to the invention is a polynucleotide, said lipid then making it possible to improve the transfecting power of the polynucleotide in a cell.

The term "polynucleotide" is intended to denote a DNA and/or RNA fragment which is double-stranded or single-stranded, linear or circular, natural, isolated or synthetic, denoting a precise sequence of nucleotides, which are modified or otherwise (see, for example, U.S. Pat. No. 5,525,711) and labeled or otherwise (see, for example, U.S. Pat. No. 4,711,955 or EP 302,175), making it possible to define a fragment or a region of a nucleic acid without size limitation. The term "polynucleotide" is intended in particular to denote a cDNA, a genomic DNA, a plasmid DNA, a messenger RNA, an antisense RNA, a ribozyme, a transfer RNA, a ribosomal RNA or a DNA coding for such RNAs. "Polynucleotide" and "nucleic acid" are synonymous terms in the context of the present application. The term "antisense" is intended to denote a nucleic acid having a sequence complementary to the target sequence, for example an mRNA sequence whose expression it is desired to block by hybridization on the target sequence; and the term "sense" is intended to denote a nucleic acid having a homologous or identical sequence to a target sequence, for example a sequence which binds to a protein transcription factor and is involved in the expression of a given gene.

According to a specific embodiment of the invention, said polynucleotide comprises a gene of interest and components allowing the expression of said gene of interest. In this embodiment, said polynucleotide is advantageously in the form of a plasmid. The components allowing expression are all the components allowing the transcription of said DNA fragment into RNA (antisense RNA or mRNA) and the translation of the mRNA into a polypeptide. They are in particular promoter sequences and/or regulatory sequences which are effective in said cell, and optionally the sequences required to allow excretion or expression of said polypeptide at the surface of the target cells. By way of example, mention will be made of promoters such as the promoters of the viruses RSV, MPSV, SV40, CMV or 7.5 k, of the vaccinia virus, the promoters of the gene coding for muscle creatine kinase, actin, or pulmonary surfactant. It is also possible to choose a promoter sequence which is specific for a given cell type or which can be activated under defined conditions. The literature provides a large amount of information relating to such promoter sequences. Moreover, said polynucleotide can comprise at least two sequences, which may be identical or different, exhibiting transcriptional promoter activity and/ or at least two coding DNA sequences, which may be identical or different, situated, relative to each other, contiguously, far apart, in the same direction or in the opposite direction, provided that the transcriptional promoter function or the transcription of said sequences is not affected. Likewise, it is possible to introduce into this type of nucleic acid construct "neutral" nucleic acid sequences or introns which do not affect transcription and are spliced before the translation step. Such sequences and their uses are described in the literature. Said polynucleotide may also contain sequences required for intracellular transport, for replication and/or for integration. Such sequences are well known to those skilled in the art. Moreover, the polynucleotides according to the present invention may also be polynucleotides which are modified such that it is not possible for them to become integrated into the genome of the target cell, or polynucleotides which are stabilized with the aid of agents such as, for example, spermine.

In the context of the present invention, the polynucleotide may be homologous or heterologous to the target cell. It may be advantageous to use a polynucleotide which codes for all or part of a polypeptide, in particular a polypeptide with therapeutic or prophylactic activity, and more particularly immunogenic activity of cellular or humoral type. The term polypeptide is understood without restriction as to its size or its degree of modification (for example glycosylation). Mention may be made, for example, of the genes coding for an enzyme, a hormone, a cytokine, a membrane receptor, a structural polypeptide, a polypeptide forming a membrane channel, a transport polypeptide, an adhesion molecule, a ligand, a factor for regulation of transcription, of translation, of replication or of stabilization of the transcripts, or an antibody, such as for example the gene coding for the CFTR protein, dystrophin, factor VIII or IX, E6/E7 of HPV, MUC1, BRAC1, β-interferon, γ-interferon, interleukin (IL) 2, IL-4, IL-6, IL-7, IL-12, tumor necrosis factor (TNF) type alpha, GM-CSF (Granulocyte Macrophage Colony Stimulating Factor), the Herpes Simplex virus type 1 (HSV-1) tk gene, the gene associated with retinoblastoma or p53 or all or part of immunoglobulins, such as the fragments F(ab)$_2$, Fab', Fab or the antiidiotypes (U.S. Pat. No. 4,699,880). Needless to say, this list is not limiting and other genes may be used.

According to a preferred embodiment, the complexes according to the invention are small in size (less than 500 nm, advantageously less than 200 nm and preferably less than 100 nm).

Moreover, the transfection experiments carried out show that, advantageously, the weight ratio of the lipid to said polynucleotide is from 0.01 to 100. The optimum ratio is from 0.05 to 10.

The invention also relates to a process for preparing cationic lipid/therapeutically active anionic substance complexes, said process being characterized in that one or more lipids in cationic form as described according to the invention are placed in contact with one or more active substances and in that said complex is recovered. The invention also relates to kits for preparing such complexes comprising one or more lipids or one or more compositions according to the invention.

In a first stage, according to a first variant, one or more cationic lipids are dissolved in a suitable amount of water-miscible solvent or solvent mixture, in particular ethanol, dimethyl sulfoxide (DMSO) or, preferably, a 1:1 (v:v) ethanol/DMSO mixture, so as to form lipid aggregates according to a known method described, for example, in patent application WO-A-96/03977, or, according to a second variant, are suspended with a suitable amount of a solution of a detergent, for instance an octyiglucoside such as n-octyl-β-D-glucopyranoside or 6-O-(N-heptylcarbomoyl)-methyl-α-D-glucopyranoside.

The suspension can then be placed in a buffer medium and mixed with a solution of therapeutically active substance containing negative charges.

When it is desired for a neutral or zwitterionic lipid to be present in the final complex, a film is formed, in a known manner, prior to the dissolution in the water-miscible solvent or in the detergent solution, with a mixture containing a said cationic lipid and a said neutral or zwitterionic lipid, such as, for example, DOPE.

One of the important characteristics of the process consists in the choice of the ratio between the positive charges of the cationic lipid and the negative charges of the active substance.

Without wishing to be limited by a specific ratio, quantities of the different charges will be chosen so that the ratio between the number of positive charges in the cationic lipid and the number of negative charges in the therapeutically active substance is between 0.05 and 20, in particular between 0.1 and 15, and preferably between 5 and 10.

The calculation to arrive at such a ratio will take into consideration the negative charges borne by the active substance and the amount of cationic lipid needed to satisfy the ratio indicated above will be adjusted. The amounts and the concentrations for the other components are adjusted according to their respective molar masses and the number of their positive and/or negative charges.

In the case of the second variant and optionally, subsequent dialysis can be carried out in order to reduce the detergent and to recover the complexes. The principle of such a method is described, for example, by Hofland et al. (1996, PNAS 93, p 7305–7309) and in chapter II of the Philippot et al. document (G. Gregoriadis, 81–89, CRC Press 1993).

It has been shown that the first variant leads to excellent results in terms of the size of the complexes obtained.

According to a third variant, one or more cationic lipids are suspended in a buffer and the suspension is then subjected to sonication until visual homogeneity is obtained. The lipid suspension is then extruded through two microporous membranes under appropriate pressure. The lipid suspension is then mixed with a solution of a therapeutically active substance comprising negative charges. This so-called sonication-extrusion technique is well known in the art.

The use of a neutral or zwitterionic lipid, such as DOPE, may prove advantageous for the production of complexes which are small in size (less than 200 nm, preferably less than 100 nm).

The characteristics of the complexes formed can be evaluated by several means which make it possible to determine, for example:

the state of complexation with the active substance, in particular by identification of the free nucleic acids by gel electrophoresis when the substances are nucleic acids, the size of the particles by quasi-elastic light scattering, the absence of long-term precipitation.

A subject of the present invention is also the complexes obtained using the processes listed above.

The invention also relates to the use of a complex according to the invention for transferring at least one therapeutically active substance, more particularly a nucleic acid, into target cells, in vitro, ex vivo or in vivo, more particularly in vivo.

According to the invention, the term "target cells" means prokaryotic cells, yeast cells and eukaryotic cells, plant cells, human or animal cells, and in particular mammalian cells. Cancer cells should moreover be mentioned. In vivo, the invention can be applied at the level of the interstitial or luminal space of tissues such as the lungs, trachea, skin, muscle, brain, liver, heart, spleen, bone marrow, thymus, bladder, lymph, blood, pancreas, stomach, kidney, ovaries, testicles, rectum, peripheral or central nervous system, eyes, lymphoid organs, cartilages and endothelium. According to an advantageous choice of the invention, the target cell will be a muscle cell, a hematopoietic stem cell or alternatively a cell of the airways, more particularly a tracheal or pulmonary cell, and advantageously a cell of the respiratory epithelium.

The complexes according to the invention can be used as a medicinal product for curative, preventive or vaccinal purposes. Accordingly, a subject of the invention is also the complexes of the invention as a medicinal product for curative, preventive or vaccinal purposes. Such complexes can be used in a therapeutic treatment method which consists in transferring at least one therapeutically active substance, in particular a polynucleotide, into target cells, in particular a mammalian cell, and more precisely a muscle cell, a hematopoietic stem cell, a cell of the airways, more particularly a tracheal or pulmonary cell, a cell of the respiratory epithelium.

More broadly, the present invention also relates to a process for introducing a therapeutically active substance comprising negative charges into a cell, characterized in that cells cultured on a suitable medium are placed in contact with a suspension of complexes of cationic lipid/ therapeutically active substance containing negative charges. After a certain incubation time, the cells are washed and recovered. The introduction of the therapeutically active substance can be checked (optionally after lysis of the cell) by any appropriate means.

The process of introduction is well known per se. The term "introduction" is understood to mean that the therapeutically active substance containing negative charges is transferred into the cell and is located, at the end of the process, inside said cell or in its membrane. When the therapeutically active substance is a nucleic acid, reference will be made more particularly to "transfection". In this case, the transfection of the nucleic acid can be checked by any appropriate means, for example by measuring the expression of the gene in question or the concentration of the expressed protein.

The invention relates more particularly to the use of a complex or of a composition according to the invention for the preparation of a medicinal product for curative, preventive or vaccinal purposes, intended for treating the human or animal body, in particular by gene therapy.

According to a first possibility, the medicinal product can be administered directly in vivo (for example into a muscle, into the lungs by aerosol and the like). It is also possible to adopt the ex vivo approach, which consists in collecting cells from the patient (bone marrow stem cells, peripheral blood lymphocytes, muscle cells and the like), transfecting them in vitro according to the present invention and readministering them to the patient.

The complexes according to the invention can be administered via the intramuscular, intratracheal, intranasal, intracerebral, intrapleural, intratumoral, intracardiac, intragastric, intraperitoneal, epidermal, intravenous or intraarterial route by syringe or by any other equivalent means, systems suitable for the treatment of the airways or of the mucous membranes such as inhalation, instillation or aerosolization. Mention may also be made of the modes of administration by applying a cream, by oral administration or any other means which is entirely known to a person skilled in the art and applicable to the present invention.

It is also within the scope of the invention to target specific organs or tissues by administering, in particular via the intravenous route, a complex according to the invention prepared so as to adjust the compounds or composition/ therapeutically active substance ratio in said complex, the apparent charge of the complex (see in particular Liu et al, 1997, Gene Therapy, 4, 517–523; Thierry et al., 1995, P.N.A.S., 92, 9742–9746).

The invention also relates to a gene therapy process which consists in administering a suitable amount of a complex according to the invention to a patient. According to the present invention and in the context of an in vivo gene therapy, it is possible to repeat the process as proposed several times, in a given patient, without any major immune reaction being triggered against one of the compounds administered. The administration can take place in a single dose or repeated once or several times after a certain time interval. Repeated administration would make it possible to reduce the amount of therapeutically active substance, more particularly of DNA, to be administered for a given dose. The appropriate route of administration and dosage vary according to various parameters, for example the individual or disease to be treated or alternatively the polynucleotide to be transferred.

The invention relates more particularly to a pharmaceutical preparation comprising at least one complex as described above, optionally also containing at least one adjuvant capable of stabilizing said pharmaceutical preparation for the purpose of storing it, for example, and/or of enhancing the transfecting power of said complex. Such an adjuvant could be chosen, for example, from the group consisting of chloroquine, a polar protic compound chosen in particular from propylene glycol, polyethylene glycol, glycerol, ethanol, 1-methyl-L-2-pyrrolidone or derivatives thereof, or a polar aprotic compound chosen in particular from dimethyl sulfoxide (DMSO), diethyl sulfoxide, di-n-propyl sulfoxide, dimethyl sulfone, sulfolane, dimethylformamide, dimethylacetamide, tetramethylurea and acetonitrile, or derivatives thereof. Likewise, said preparation can contain a pharmaceutically acceptable support allowing its administration to humans or animals.

In the context of the use of an in vivo treatment process according to the present invention, it is also possible, before administering a pharmaceutical preparation as described above, to carry out a treatment on the patient which is designed to observe a temporary depletion of the macrophages making it possible to enhance the level of transfection. Such a technique is described in the literature; see in particular Van Rooijen et al., 1997, TibTech, 15, 178–184.

Finally, the invention relates to a cell transfected with a complex as defined above, particularly a prokaryotic cell, a yeast cell or eukaryotic cell, especially an animal cell, in particular a mammalian cell, and more particularly a cancer cell. According to a preferred case of the invention, said cell is a cell of the airways, more particularly a tracheal or pulmonary cell, and advantageously a cell of the respiratory epithelium.

The examples below illustrate the invention without limiting it in any way.

BRIEF DESCRIPTION OF THE DRAWINGS

FIG. 1: pcTG51 in the absence of DOPE.

FIG. 2: pcTG51 in the presence of an equimolar amount of DOPE.

FIG. 3: pcTG52 in the absence of DOPE.

FIG. 4: pcTG52 in the presence of an equimolar amount of DOPE.

FIG. 5: pcTG53 in the absence of DOPE.

FIG. 6: pcTG53 in the presence of an equimolar amount of DOPE.

FIG. 7: pcTG54 in the absence of DOPE.

FIG. 8: pcTG54 in the presence of an equimolar amount of DOPE.

FIG. 9: pcTG57 with or without DOPE.

FIG. 10: pcTG58 with or without DOPE.

FIG. 11: pcTG59 in the absence of DOPE.

FIG. 12: pcTG59 in the presence of an equimolar amount of DOPE.

FIG. 13: pcTG60 in the absence of DOPE.

FIG. 14: pcTG60 in the presence of an equimolar amount of DOPE.

Figure 1:
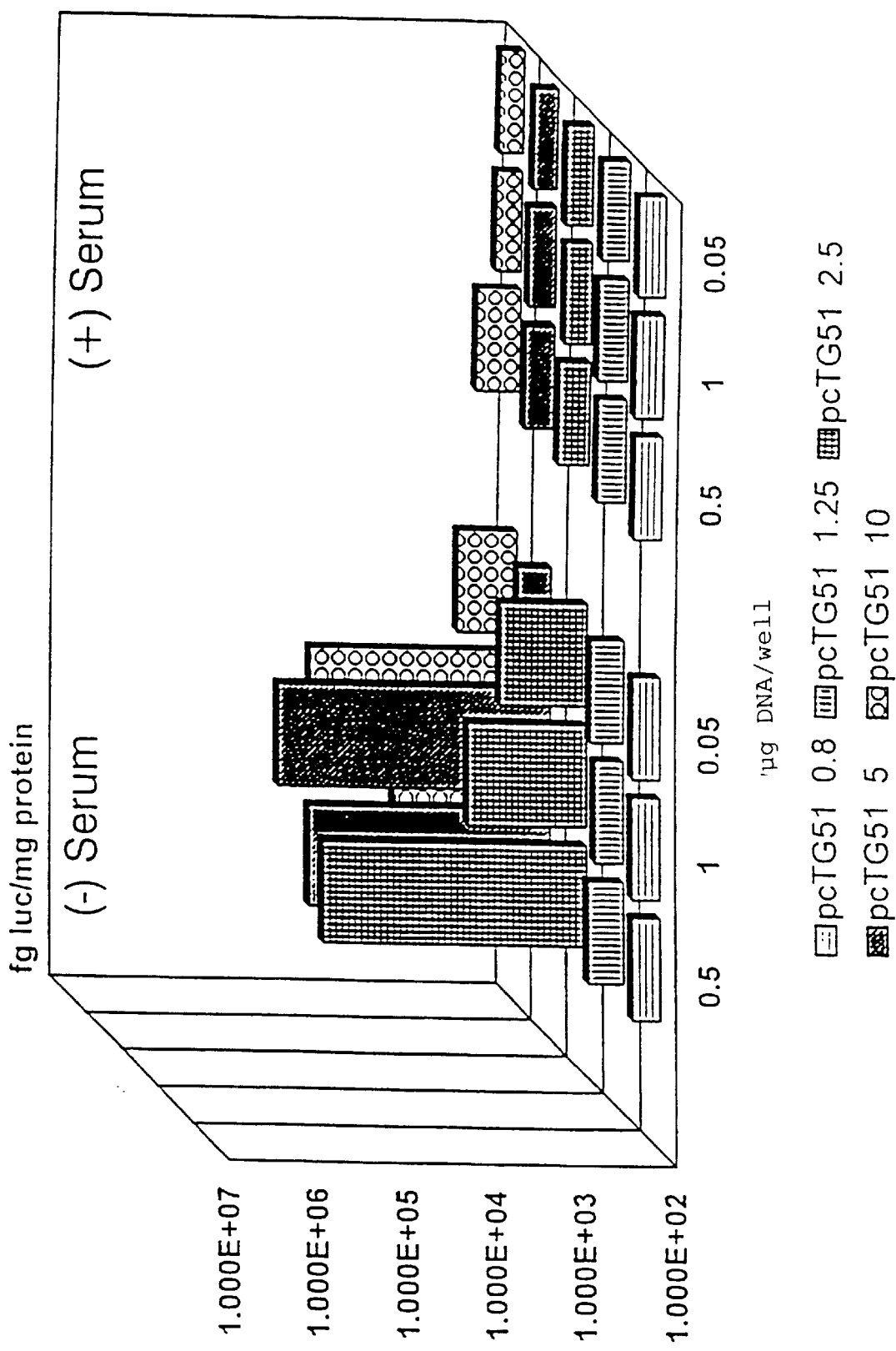
FIGS. 1 to 14: in vitro transfection of A549 cells with various DNA/cationic lipid complexes according to the invention.

For each of the figures, the presence or absence of fetal calf DOPE is indicated as (+) and (6) [sic] respectively; the amount of the plasmid DNA per well is indicated on the x-axis (0.5, 1 or 0.05 μg/well); the charge ratios are indicated in the keys (0.8, 1.25, 2.5, 5 or 10); the luciferase activity measured, expressed as fg of luciferase/mg of total protein, is indicated on the y-axis.

EXAMPLE 1

Synthesis of the cationic lipid pcTG23 of formula I in which $n_1=n_2=0$, $R_3$, $R_4$ an ethylene chain m=p= 3, $R_5=R_6=$NHCO $C_{13}H_{27}$ A solution of dicylcohexylcarbodiimide (2.06 g; 9.98 mmol) in dry chloroform (5 ml) is added to a solution of 1,4-bis(3-aminopropyl)piperazine (1.00 g; 5.00 mmol), myristic acid (2.28 g; 9.98 mmol) and 1-hydroxybenzotriazole (1.42 g; 10.5 mmol) in dry chloroform (15 ml). The reaction mixture is stirred for 4 h at room temperature and then filtered to remove the dicyclohexylurea. The filtrate is concentrated under reduced pressure and chromatographed on a column of silica gel (eluent: 9/1 dichloromethane/methanol) to give the diamide pcTG23 (2.7 g; 87%) with a melting point of 117–118° C.

$^1$H NMR (200 MHz, CDCl$_3$): δ6.87 (broad t, J=5.5 Hz, 2H, —NH—C(O)—); 3.3 (q, J=5.9 Hz, 4H, —$\underline{CH_2}$—NH—C(O)—); 2.65–2.37 (m and t, J=6.3 Hz, 12H, —$\underline{CH_2}$—N); 2.13 (t, J=7.6 Hz, 4H, —CH$_2$—C(O)—), 1.75–1.50 (m and quint., J=6.3 Hz, 8H, —$\underline{CH_2}$—CH$_2$—C(O)— and —$\underline{CH_2}$—CH$_2$—NH—); 1.25 (s, 40H, —CH$_2$—); 0.87 (t, J=6.4 Hz, ′6H, Me–).

Mass spectrometry: calculated mass=621.1 Da; measured mass=620.6 Da.

EXAMPLE 2

Synthesis of the cationic lipid pcTG24 of formula I in which $R_1=R_2=$methyl; $R_3$ and $R_4$ together form an ethylene residue; m=3; p=3; $R_5$ and $R_6$ are NH C(=O) $C_{13}H_{27}$ radicals (n-tridecyl residue $C_{13}H_{27}$)

0.5 ml of iodomethane (8.0 mmol) and a suspension of diamide pcTG23 (100 mg; 0.16 mmol) in 4 ml of acetonitrile are refluxed for 40 h, cooled to room temperature and diluted in 20 ml of ether. The suspension thus obtained is filtered to give a pale yellow powder which is washed with ether and dried under vacuum. After recrystallization from a chloroform/methanol mixture, the cationic lipid pcTG24 of formula I (135 mg; 93%) is obtained, the melting point of which is 198° C.

$^1$H NMR (200 MHz, CDCl$_3$-CF$_3$CO$_2$D): δ4.30–4.00 (m, 12H, —CH$_2$—N$^+$), 3.54 (broad s, 10H, —$\underline{CH_2}$—NH—CO— and Me—N$^+$), 2.48 and 2.44 (2 t, J=7.5 Hz, 4H, —CH$_2$—CO—), 2.22 (m, 4H —$\underline{CH_2}$—CH$_2$—NH—CO—), 1.62 (m, 4H, —$\underline{CH_2}$—CH$_2$—CO—), 1.25 (s, 40H, —$\underline{CH_2}$—), 0.88 (t, J=6.4 Hz, 6H, Me⁻).

Mass spectrometry: calculated 651.2 Da, found 650.6 Da; analysis calculated for $C_{40}H_{82}I_2N_4O_2$: C, 53.09%, H, 9.13%; N, 6.19%. Found: C, 53.1%; H, 9.1%; N, 6.2%.

EXAMPLE 3

Synthesis of the cationic lipid pcTG40 of formula I in which $R_3$, $R_4$=ethylene chain; $R_1$, $R_2$=methyl; m=p=1; $R_5=R_6=(C_8H_{17})_2$NC(=O)

Synthesis of 2-bromo-N,N-dioctylacetamide (cf.: Li, T.; Diederich, F. J. Org. Chem. 1992, 57, 3449–3454).

A solution of bromoacetyl bromide (0.69 ml; 7.94 mmol) in tetrahydrofuran (2 ml) at 0° C. is added to a mixture of dioctylamine (2.00 ml; 6.62 mmol) and diisopropylethylamine (1.73 ml; 9.93 mmol) in tetrahydrofuran (13 ml). The mixture is stirred for 1 h at room temperature and is then diluted with ether (25 ml) and washed with aqueous 10% hydrochloric acid solution (10 ml).

The organic phase is washed with water, dried over sodium sulfate, concentrated under reduced pressure and purified by chromatography on a column of silica gel (eluent: 85/15 hexane/ether) to give 2-bromo-N,N-dioctylacetamide (2.23 g; 93%) in the form of a brown oil.

1H NMR (200 MHz, CDCl$_3$): δ3.83 (s, 2H, BrCH$_2$—C(O)—); 3.31 and 3.27 (2t, J=6.5 Hz, 4H, —CH$_2$)$_2$N—C(O)—); 1.57 (m, 4H, —CH$_2$—CH$_2$)$_2$N—C(O)—); 1.28 (s, 20H, —CH$_2$—): 0.89 and 0.87 (2t, J=6.4 Hz, 6H, Me–).

Cationic lipid pcTG40

A solution of N,N'-dimethyl-1,4-piperazine (30 mg; 0.26 mmol) and 2-bromo-N,N-dioctylacetamide (200 mg; 0.55 mmol) in acetonitrile (2 ml) is refluxed for 16 h. The solution is concentrated under reduced pressure and the residue is purified by chromatography on a column of silica gel (eluent: 95/5 and then 90/10 dichloromethane/methanol) to give the cationic lipid pcTG40 (166 mg; 76%) with a melting point of 169–170° C.

1H NMR (200 MHz, CDCl$_3$): δ5.38 (s, 4H, N$^+$—CH$_2$—C(O)—); 5.00–4.87 and 4.78–4.65 (2m, 8H, —CH$_2$—N$^+$); 4.01 (s, 6H, Me—N$^+$); 3.40–3.20 (m, 8H, —CH$_2$)$_2$N—C(O); 1.53 (m, 8H, —CH$_2$—CH$_2$)$_2$N—C(O)$^-$); 1.27 (broad s, 40H, —CH$_2$—); 0.88 (t, J=6.4 Hz, 12H, Me–).

Mass spectrometry: calculated mass=679.2 Da; measured mass =678.8 Da.

EXAMPLE 4

Synthesis of the cationic lipid pcTG42 of formula I in which $R^1$=$R_2$=$R_3$=$R_4$=methyl; m=p=1; $R_5$=$R_6$=C(=O)—N($C_8H_{17}$)$_2$, ($C_8H_{17}$)=n-octyl The same procedure as for the cationic lipid pcTG40 allows the preparation of the cationic lipid pcTG42 (498 mg; 92%) in the form of a wax, starting with N,N,N',N'-tetramethylethylenediamine (75 mg; 0.64 mmol) and 2-bromo-N,N-dioctylacetamide (700 mg; 1.93 mmol).

$^1$H NMR (200 MHz, CDCl$_3$): δ5.13 (s, 4H, N$^+$—CH$_2$—C(O)—); 4.84 (s, 4H, —CH$_2$—N$^+$); 3.72 (s, 12H, Me—N$^+$); 3.30 (m, 8H, —CH$_2$)$_2$N—C(O)—); 1.75–1.45 (m, 8H, —CH$_2$—CH$_2$)$_2$N—C(O)—); 1.28 (s, 40H, —CH$_2$—); 0.88 (t, J=6.4 Hz, 12H, Me–).

Mass spectrometry: calculated mass=681.2 Da; measured mass=681.0 Da.

EXAMPLE 5

Synthesis of the cationic lipid pcTG30 of formula I in which $n_1$=$n_2$=0, $R_3$, $R_4$ ethylene chain, m=p=3, $R_5$=$R_6$=HN—(O=)C—$C_{17}H_{33}$ The same procedure as for the diamide pcTG23 allows the preparation of the diamide pcTG30 (1.09 g; 84%) with a melting point of 79° C., starting with 1,4-bis(3-aminopropyl)piperazine (0.355 g; 1.77 mmol) and oleic acid (1.00 g; 3.54 mmol) in the presence of 1-hydroxybenzotriazole (0.502 g; 3.72 mmol) and dicyclohexylcarbodiimide (1.10 g; 5.31 mmol).

1H NMR (200 MHz, CDCl$_3$): δ6.79 (t, J=5 Hz, 2H, —NH—C(O)—); 5.33 (m, 4H, —CH=); 3.33 (q, J=5.9 Hz, 4H, —CH$_2$—NHC(O)—); 2.88–2.38 (m and t, J=6.3 Hz, 12H, —CH$_2$—N—); 2.13 (t, J=7.5 Hz, 4H, —CH$_2$—C(O)—), 2.00 (m, 8H, —CH$_2$—CH=); 1.78–1.52 (m and quint., J=6.3 Hz, 8H, —CH$_2$—CH$_2$—C(O)— and —CH$_2$—CH$_2$—NH); 1.30 and 1.26 (2s, 40H, —CH$_2$—); 0.87 (t, J=6.4 Hz, 6H, Me–).

Mass spectrometry: calculated mass=729.2 Da; measured mass=728.7 Da.

EXAMPLE 6

Synthesis of the cationic lipid pcTG38 of formula I in which $R_1$=$R_2$=methyl; $R_3$, $R_4$ ethylene chain; m=p=3; $R_5$=$R_6$=HN—(O=)C—$C_{17}H_{33}$ The same procedure as for the cationic lipid pcTG24 allows the preparation of the cationic lipid pcTG38 (135 mg; 97%) with a melting point of 175–180° C. (decomposition), starting with diamide pcTG30 (100 mg; 0.137 mmol) suspended in acetonitrile (4 ml) and methyl iodide (0.5 ml; 8.0 mmol).

$^1$H NMR (200 MHz, CDCl$_3$, CF$_3$CO$_2$D); 5.35 (m, 4H, —CH=); 4.35–3.90 (m, 12H, —CH$_2$—N$^+$); 3.58 (t, J=5.8 Hz, 4H, —CH$_2$—NH—C(O)—); 3.48 and 3.45 (2s, 6H, —Me—N$^+$); 2.49 (t, J=7.7 Hz, 4H, —CH$_2$—C(O)—): 2.20 (m, 4H, —CH$_2$—CH$_2$—N$^+$); 2.01 (m, 8H, —CH$_2$—CH=) 1.57–1.75 (m, 4H, —CH$_2$—CH$_2$—C(O)—); 1.30, 1.29 and 1.27 (3s, 40H, —CH$_2$—); 0.87 (t, J=6.2 Hz, 6H, —Me).

Mass spectrometry: calculated mass=759.3 Da; measured mass=759.0 Da.

EXAMPLE 7

Cationic lipid pcTG51 of formula I in which $R_1$=$R_2$=methyl; $R_3$, $R_4$ ethylene chain; m=p=1; $R_5$=($C_{14}H_{29}$)$_2$ NC(O); $R_6$=H a) A solution of N,N'-dimethyl-1,4-piperazine (0.13 g; 1.13 mmol) in acetonitrile is added slowly to a solution of 2-bromo-N,N-ditetradecylacetamide (0.30 g; 0.56 mmol) in acetonitrile (5 ml). Next, the reaction mixture is stirred at room temperature for 0.5 h, and then at 40° C. for 1 h. The acetonitrile and the excess N,N'-dimethyl-1,4-piperazine are evaporated off under reduced pressure.

b) Iodomethane (1 ml) is added to a solution in acetonitrile (5 ml) of the residual liquid obtained above. The mixture is refluxed for 4 h and then, after cooling, ether (2 ml) is added. The white precipitate which then forms is filtered off on paper and then purified by chromatography on a column of silica gel (eluent: 15/85 methanol/dichloromethane) to give the cationic lipid pcTG51 (0.41 g; 92%) in the form of a white solid.

Melting point m.p.=168–170° C. (decomposition).

1H NMR (200 MHz, CDCl$_3$-CF$_3$CO$_2$D): δ4.93 (s, 2H, >N$^+$(Me)—CH$_2$—C(O)—); 4.80 and 4.50–4.00 (2m, 2H and 6H, Me$_2$N$^+$(CH$_2$—CH$_2$)$_2$N$^+$(Me)—); 3.69 (s, 3H, >N$^+$(Me)—CH$_2$—CO(O)—); 3.58 and 3.53 (2s, 6H, Me$_2$N$^+$<) 3.32 (m, 4H, —CH$_2$)$_2$N—C(O))—; 1.59 (m, 4H, —CH$_2$—CH$_2$)$_2$N—C(O)—)—; 1.26 (s, 44H, —CH$_2$—): 0.88 (t, J=6.4 Hz, 6H, Me–).

EXAMPLE 8

Cationic lipid pcTG52 of formula I in which $R_1$=$R_2$=$R_3$=$R_4$=methyl; m=p=1; $R_5$=($C_{14}H_{29}$)$_2$NC(O); $R_6$=H The same procedure as for the cationic lipid pcTG51 allows the preparation of the cationic lipid pcTG52 (0.42 g;

94%) in the form of a white solid, starting with N,N,N',N'-tetramethylethylenediamine (0.13 g; 1.13 mmol), 2-bromo-N,N-ditetradecylacetamide (0.30 g; 0.57 mmol) and iodomethane (1 ml).

Melting point m.p.: 125–126° C. (decomposition)

$^1$H NMR (200 MHz, CDCl$_3$-CF$_3$CO$_2$D): δ4.85 (m, 2H, —CH$_2$—N$^+$(Me$_2$)—); 4.75 (s, 2H, —N$^+$(Me$_2$)—CH$_2$—C(O)—N<); 4.53 (m, 2H, Me$_3$N$^+$—CH$_2$—); 3.62 (s, 6H, —N$^+$(Me$_2$)—); 3.41 (s, 9H, Me$_3$N$^+$—); 3.30 (m, 4H, —CH$_2$)$_2$N—C(O)—); 1.57 (m, 4H, —CH$_2$—CH$_2$)$_2$N—C(O)—); 1.26 (s, 44H, —CH$_2$—); 0.88 (t, J=6.4 Hz, 6H, Me-).

EXAMPLE 9

Cationic lipid pcTG53 of formula I in which $R_1=R_2=$2-hydroxyethyl $R_3=R_4=$ethylene chain; m=p=1; $R_5=(C_{14}H_{29})_2$ NC(O); $R_6=$H A solution of 1,4-bis (2-hydroxyethyl)piperazine (0.33 g; 1.88 mmol) and 2-bromo-N,N-ditetradecylacetamide (0.50 g; 0.94 mmol) in acetonitrile is stirred for 1 h at room temperature. The mixture is then concentrated under reduced pressure and the residue is chromatographed on a column of silica gel (eluent: 10/90 and then 15/85 methanol/dichloromethane) to give the monoalkylation product (0.67 g) which is taken up in acetonitrile (5 ml) and refluxed for 4 h in the presence of iodomethane (1 ml). The suspension thus obtained is then left to cool, diluted with ether and filtered, which gives a white powder which is washed with ether and dried under vacuum. After chromatography on a column of silica gel (eluent: 15/85 methanol/dichloromethane), the cationic lipid pcTG53 (0.59 g; 74%) is obtained in the form of a white solid.

Melting point m.p.: 156–158° C.

$^1$H NMR (200 MHz, CDCl$_3$-CF$_3$CO$_2$D): δ5.21 (s, 2H, N$^+$—CH$_2$—C(O)—N<); 4.90–4.10 (m, 16H, —N$^+$(CH$_2$—CH$_2$—OH) (CH$_2$—CH$_2$)$_2$N$^+$(Me)CH$_2$—CH$_2$—OH); 3.73 and 3.67 (2s, 3H, —N$^+$(Me)—, 2 stereoisomers); 3.31 (m, 4H, —CH$_2$)$_2$N—C(O)—); 1.58 (m, 4H, —CH$_2$—CH$_2$)$_2$N—C(O)—); 1.26 (s, 44H, —CH$_2$—); 1.26 (s, 44H, —Ch$_2$—); 0.88 (t, J=6.4 Hz, 6H, Me-).

EXAMPLE 10

Cationic lipid pcTG54 of formula I in which $R_1=R_2=$methyl; $R_3=R_4=$ethylene chain; m=p=1; $R_5=$(C18H35)2 NC(O); $R_6=$H The same procedure as for the cationic lipid pcTG51 allows the preparation of the cationic lipid pcTG54 (254 mg; 93%) in the form of a yellowish solid, starting with N,N'-dimethyl-1,4-piperazine (66 mg; 0.58 mmol), 2-iodo-N,N-dioleylacetamide (200 mg; 0.29 mmol) and iodomethane (0.5 ml).

Melting point m.p.: 155–160° C. (decomposition).

$^1$H NMR (200 MHz, CDCl$_3$-CF$_3$CO$_2$D): δ5.36 (m, 4H, —CH=); 5.11 (s, 2H, >N$^+$(Me)CH$_2$—C(O)—N<); 4.82 and 4.60–4.00 (2m, 2H and 6H, Me$_2$N$^+$(CH$_2$—CH$_2$)$_2$N$^+$(Me)—); 3.79 (s, 3H, >N$^+$(Me)CH$_2$C(O)—N<); 3.66 and 3.62 (2s, 6H, Me$_2$N+<); 3.33 (m, 4H, CH$_2$)$_2$N—C(O)—); 2.02 (m, 8H, —CH$_2$—CH=); 1.58 (m, 4H, —CH$_2$—CH$_2$)$_2$N—C(O)—); 1.29 and 1.28 (2s, 44H, —CH$_2$—); 0.88 (t, J=6.4 Hz, 6H, Me-).

EXAMPLE 11

Cationic lipid pcTG55 of formula I in which $R_1=R_2=R_4=$methyl; m=p=1; $R_5=$(C18H35)2 NC(O); R=H The same procedure as for the cationic lipid pcTG51 allows the preparation of the cationic lipid pcTG55 (248 mg; 91%) in the form of a yellowish paste, starting with N,N,N',N'-tetramethylethylenediamine (67 mg; 0.58 mmol), 2-iodo-N,N-dioleylacetamide (200 mg; 0.29 mmol) and iodomethane (0.5 ml).

Melting point m.p.: 125–126° C. (decomposition)

$^1$H NMR (200 MHz, CDCl$_3$): δ5.35 (m, 4H, —CH=); 5.12–4.77 (m, 4H, Me$_2$N$^+$—CH$_2$—CH$_2$—N$^+$(Me)$_2$—); 4.92 (s, 2H, —N$^+$(Me$_2$)—CH$_2$—C(O)—N<); 3.79 (s, 6H, —N$^+$(Me$_2$)—CH$_2$—C(O)—N<); 3.60 (s, 9H, Me$_3$N$^+$—); 3.32 (m, 4H, —CH$_2$)$_2$N—C(O)—); 2.01 (m, 8H, —CH$_2$—CH=); 1.58 (m, 4H, —CH$_2$—CH$_2$)$_2$N—C(O)—); 1.29 and 1.27 (2s, 44H, —CH$_2$—); 0.88 (t, J=6.4 Hz, 6H, Me-).

EXAMPLE 12

Cationic lipid pcTG50 in which $R_1=R_2=$2 methyl; $R_3=R_4=$ethylene chain; m=p=1; $R_5=(C_8H_{17})_2$ NC(O); $R_6=$H The same procedure as for the cationic lipid pcTG51 allows the preparation of the cationic lipid pcTG50 (0.36 g; 85%) in the form of a white solid, starting with N,N'-dimethyl-1,4-piperazine (0.16 g; 1.38 mmol), 2-bromo-N,N-dioctylacetamide (0.25 g; 0.69 mmol) and iodomethane (0.5 ml).

Melting point m.p.=175° C. (decomposition)

$^1$H NMR (200 MHz, CDCl$_3$—CD$_3$OD—CF$_3$CO$_2$D): δ5.04 (s, 2H, >N$^+$(Me)—CH$_2$—C(O)—N<); 4.72 and 4.50–4.00 (2m, 2H and 6H, Me$_2$N$^+$(CH$_2$—CH$_2$)$_2$N$^+$(Me)—); 3.74 (s, 3H, >N$^+$(Me)—); 3.61 (s, 6H, Me$_2$N$^+$<); 3.27 (m, 4H, —CH$_2$)$_2$N—C(O)—); 1.54 (m, 4H, —CH$_2$—CH$_2$)$_2$N—C(O)—); 1.24 (s, 20H, —CH$_2$—); 0.84 (t, J=6.4 Hz, 6H, Me-).

The starting compounds for the synthesis of pcTG50 to pcTG55 are prepared in the following way:

N,N-ditetradecyl-p-toluenesulfonamide

Potassium carbonate (20.18 g; 146.00 mmol) is added to a solution of p-toluenesulfonamide (5.00 g; 29.20 mmol) and 1-bromotetradecane (21.70 ml; 73.00 mmol) in dimethylformamide (75 ml). The suspension is stirred for 20 h at reflux; the reaction medium is then cooled to room temperature, diluted with ether (100 ml) and filtered. The filtrate is washed with water (50 ml) and the aqueous phase is extracted with ether (100 ml). The combined organic phases are dried over sodium sulfate, filtered and concentrated under reduced pressure to give a white solid which is purified by chromatography on a column of silica gel (eluent: 40/60 dichloromethane/hexane) to give N,N-ditetradecyl-p-toluenesulfonamide (15.86 g; 96%) in the form of a white solid.

Melting point m.p.=54° C. 1H NMR (200 MHz, CDCl$_3$): δ7.68 (d, J=8.3 Hz, 2H, aromatic H); 7.28 (d, J=8.3 Hz, 2H, aromatic H); 3.08 (apparent t, J=7.6 Hz, 4H, —CH$_2$)$_2$NSO$_2$—); 2.42 (s, 3H, Me—Ar); 1.50 (m, 4H, —CH$_2$—CH$_2$)$_2$NSO$_2$—); 1.26 and 1.25 (2s, 44H, —CH$_2$—); 0.88 (t, J=6.4 Hz, 6H, Me-).

Ditetradecylamine

A solution of N,N-ditetradecyl-p-toluenesulfonamide (4.16 g; 7.38 mmol) in tetrahydrofuran (2 ml) is added at 0° C. to a solution of lithium naphthalenide [prepared from naphthalene (4.73 g; 36.88 mmol) and lithium metal (0.38 g; 55.35 mmol) in tetrahydrofuran (40 ml) at room temperature for 1 h] and the reaction mixture is stirred for 1 h at room temperature. Methanol (2 ml) is added, followed by water (25 ml) and the mixture is extracted with ether (2×25 ml). The organic phase is dried over sodium sulfate, filtered and concentrated under reduced pressure to give a white solid which is purified by chromatography on a column of silica gel (eluent: ether) to give ditetradecylamine (2.68 g; 89%).

$^1$H NMR (200 MHz, CDCl$_3$): δ2.58 (t, J=7.1 Hz, 4H, —CH$_2$)$_2$NH—); 1.48 (m, 5H, —CH$_2$—CH$_2$)$_2$NH—); 1.26 (s, 44H, —CH$_2$—); 0.88 (t, J=6.4 Hz, 6H, Me-).

2-Bromo-N,N-ditetradecylacetamide

The same procedure as for 2-bromo-N,N-dioctylacetamide allows the preparation of 2-bromo-N,N-ditetradecylacetamide (1.28 g; 87%) in the form of a yellowish liquid, starting with bromoacetyl bromide (0.29 ml; 3.34 mmol) and ditetradecylamine (1.10 g; 2.78 mmol).

$^1$H NMR (200 MHz, CDCl$_3$): δ3.82 (s, 2H, Br—CH$_2$—C(O)—); 3.30 and 3.26 (2t, J=6.8 Hz, 4H, —CH$_2$)$_2$N—C(O)—); 1.56 (m, 4H, —CH$_2$—CH$_2$)$_2$NC(O)—); 1.25 (s, 44H, —CH$_2$—); 0.87 (t, J=6.3 Hz, 6H, Me-).

Oleyl Bromide

Triphenylphosphine (2.52 g; 9.62 mmol) is added portionwise to a vigorously stirred solution of oleyl alcohol (1.00 g; 3.72 mmol; Fluka, 99%) and tetrabromomethane (1.61 g; 4.84 mmol) in acetonitrile (15 ml) at 0° C. The heterogeneous medium is stirred for 1 h at room temperature. The supernatant is then transferred into a round-bottomed flask and the residual paste is triturated with ether (10 ml) and then filtered. The combined organic solutions are concentrated under reduced pressure to give a colorless oil which is purified by chromatography on a column of silica gel (eluent: hexane) to give oleyl bromide (1.21 g; 98%) in the form of a colorless oil.

$^1$H NMR (200 MHz, CDCl$_3$): δ5.35 (m, 2H, —CH=); 3.41 (t, J=6.8 Hz, 2H, —CH$_2$—Br); 2.02 (m, 4H, —CH$_2$—CH=); 1.86 (quint., J=6.8 Hz, 2H, —CH$_2$—CH$_2$—Br); 1.42 (m, 2H, —CH$_2$—CH$_2$—CH$_2$—Br); 1.30 and 1.28 (2s, 20H, —CH$_2$—); 0.89 (t, J=6.4 Hz, 3H, Me-).

N,N-dioleyl-p-toluenesulfonamide

The same procedure as for N,N-ditetradecyl-p-toluenesulfonamide allows the preparation of N,N-dioleyl-p-toluenesulfonamide (0.83 g; 87%), starting with oleyl bromide (1.20 g; 3.62 mmol), p-toluenesulfonamide (0.28 g; 1.65 mmol) and potassium carbonate (1.14 g; 8.25 mmol).

$^1$H NMR (200 MHz, CDCl$_3$): δ7.68 (d, J=8.2 Hz, 2H, aromatic H); 7.28 (d, J=8.2 Hz, 2H, aromatic H); 5.35 (m, 4H, —CH=); 3.08 (apparent t, J=7.5 Hz, 4H, —CH$_2$)$_2$NSO$_2$—); 2.42 (s, 3H, Me—Ar—); 2.01 (m, 8H, —CH$_2$—CH=); 1.50 (m, 4H, —CH$_2$—CH$_2$)$_2$NSO$_2$—); 1.27 (s, 44H, —CH$_2$—); 0.88 (t, J=6.3 Hz, 6H, Me-).

Dioleylamine

The same procedure as for ditetradecylamine allows the preparation of dioleylamine (0.55 g; 71%) in the form of a yellowish oil, starting with N,N-dioleyl-p-toluenesulfonamide (1.00 g; 1.49 mmol), naphthalene (0.95 g; 7.44 mmol) and lithium metal (0.08 g; 11.18 mmol).

$^1$H NMR (200 MHz, CDCl$_3$): δ5.35 (m, 4H, —CH=) 2.58 (t, J=7.1 Hz, 4H, —CH$_2$)$_2$NH—); 2.01 (m, 8H, —CH$_2$—CH=); 1.48 (m, 5H, —CH$_2$—CH$_2$)$_2$NH—); 1.29 and 1.28 (2s, 44H, —CH$_2$—); 0.88 (t, J=6.4 Hz, 6H, Me-).

2-Bromo-N,N-dioleylacetamide

The same procedure as for 2-bromo-N,N-dioctylacetamide allows the preparation of 2-bromo-N,N-dioleylacetamide (0.83 g; 82%) in the form of a yellowish liquid, starting with bromoacetyl bromide (0.17 ml; 1.89 mmol) and dioleylamine (0.82 g; 1.58 mmol).

$^1$H NMR (200 MHz, CDCl$_3$) δ5.30 (m, 4H, —CH=); 3.78 (s, 2H, Br—CH$_2$—C(O)—); 3.26 and 3.22 (2t, J=7.0 Hz, 4H, —CH$_2$)$_2$N—C(O)—); 1.96 (m, 8H, —CH$_2$—CH=); 1.54 (m, 4H, —CH$_2$—CH$_2$)$_2$NC(O)—); 1.25 and 1.24 (2s, 44H, —CH$_2$—); 0.83 (t, J=6.3 Hz, 6H, Me-).

2-Iodo-N,N-dioleylacetamide

A solution of 2-bromo-N,N-dioleylacetamide (0.81 g; 1.27 mmol) and sodium iodide (0.76 g; 5.08 mmol) in acetone is refluxed overnight. Hexane (10 ml) is added and the precipitate is filtered off to give, after evaporating the filtrate under reduced pressure, 2-iodo-N,N-dioleylacetamide (0.87 g; 100%) in the form of a yellowish liquid.

$^1$H NMR (200 MHz, CDCl$_3$): δ5.32 (m, 4H, —CH=); 3.71 (s, 2H; I—CH$_2$C(O)—); 3.30 and 3.23 (2t, J=7.4 Hz, 4H, —CH$_2$)$_2$N—C(O)—); 2.02 (m, 8H, —CH$_2$—CH=); 1.56 (m, 4H, —CH$_2$—CH$_2$)$_2$N—C(O)—); 1.31 and 1.29 (2s, 44H, —CH$_2$—); 0.88 (t, J=6.6 Hz, 6H, Me-).

Preparation of the Lipid-DNA Complexes by Suspension in Ethanol

1. Preparation of the complexes of lipids pcTG24, optionally DOPE, -DNA, +/−charge ratio =10

The amounts of lipids are calculated on the basis of the final DNA concentration (0.1 mg/ml for the in vitro tests), the desired charge ratio, the molar mass of the lipid, the number of positive charges on the cationic lipid chosen and the desired final volume. As an example, in order to obtain 0.5 ml of a complex between pcTG24/DOPE and plasmid DNA with a charge ratio of 10 between the positive charges provided by the cationic lipid and the negative charges provided by the DNA at a final DNA concentration of 0.1 mg/ml, the various ingredients are mixed together according to the following calculation:

0.1 mg of DNA/ml, i.e. (0.1/330) mmol of negative charges (330 Da is the average molecular weight of a nucleotide) per ml correspond to 0.30 μmol/ml of negative charges or 0.15 μmol of negative charges per 0.5 ml. In order to obtain 10 times as many positive charges, a concentration of 3.0 μmol/ml of positive charges provided by the cationic lipid (1.5 μmol per 0.5 ml) is needed. The molar mass of pcTG24 in the form of the iodide salt is 905 g/mol and the molecule contains 2 positive charges.

Thus, 0.75 μmol/ml of pcTG24 are needed, which corresponds to 0.68 mg/ml. In order to have a slight excess, a suspension is prepared using 1.0 μmol (0.9 mg) of pcTG24. In order to obtain an equimolar concentration of L-α-dioleoylphosphatidylethanolamine (DOPE, 744 g/mol, Sigma; P0510), 0.74 mg/ml of this material is needed in the lipid preparation. The amounts and concentrations for the other compounds are adjusted in accordance with their respective molar masses and their number of positive charges.

The lipids are mixed using solutions in chloroform/methanol (v:v). The cationic lipids are weighed and the amount of DOPE is added using a solution of 10 or 20 mg/ml in chloroform in a glass tube, sterilized with alcohol and with UV, in order to obtain a concentration of 2 mM of cationic lipid (4 mM of total lipid). The solvents are evaporated off under vacuum (0.2×105 Pa (200 bar)) for 45 min at 45° C. using a vortex of 40 revolutions per minute (Labconco, Rapidvap, Uniequip, Martinsried, Germany). The lipid film is taken up in 18 µl of ethanol in order to be at a concentration of 50 mg/ml of cationic lipid.

This solution is completed with 162 µl of 20 mM HEPES pH 7.5 (adjusted with NaOH) in order to prepare a solution containing 5 mg/ml final of cationic lipid.

The plasmid DNA is prepared using a stock solution containing 1 mg/ml (in 10 mM Tris, 1 mM EDTA, pH 7.5).

For a solution of 0.5 ml final, 50 µl of the stock solution (50 µg DNA) are taken and 313 µl of 20 mM HEPES pH 7.5 are added thereto.

In order to complex the DNA with lipid preparations, lipids are added to the DNA. The suspension is mixed 10 times by aspiration/discharge. The complexes are stored at +4° C.

137 µl of pcTG24/DOPE are added to 363 µl of the DNA solution in order to obtain 0.5 ml of complex containing 0.1 mg/ml DNA and a charge ratio of 10.

The complexes are prepared under a laminar-flow fume cupboard. During the other steps, any contamination should also be avoided.

2. Preparation of the complexes of lipids pcTG42, optionally DOPE, -DNA in a +/–charge ratio=10

The amounts of lipids are calculated on the basis of the final DNA concentration (0.1 mg/ml for the in vitro tests), the desired charge ratio, the molar mass of the lipid, the number of positive charges on the cationic lipid chosen and the desired final volume (0.5 ml). As an example, in order to obtain 0.5 ml of a complex between pcTG42/DOPE and plasmid DNA with a charge ratio of 10 between the positive charges provided by the cationic lipid and the negative charges provided by the DNA at a final DNA concentration of 0.1 mg/ml, the calculation is as follows: 1 mg of DNA/ml, i.e. (0.1/330) mmol of negative charges (330 Da is the average molecular weight of a nucleotide) per ml correspond to 0.30 µmol/ml of negative charges or 0.15 µmol of negative charges per 0.5 ml. In order to obtain 10 times as many positive charges, a concentration of 3.0 µmol/ml of positive charges provided by the cationic lipid (1.5 µmol per 0.5 ml) is needed. The molar mass of pcTG42 in the form of the bromide salt is 841 g/mol and the molecule contains 2 positive charges. Thus, 0.75 µmol/ml of pcTG42 is needed, which corresponds to 0.63 mg/ml. In order to have a slight excess, a suspension is prepared using 1.0 µmol (0.84 mg) of pcTG42.

An equimolar concentration of DOPE (744 g/mol, Sigma; P0510) corresponds to 0.74 mg in the lipid preparation.

The lipids are mixed together as above. The lipid film is taken up in 17 µl of ethanol in order to adjust the concentration to 50 mg/ml of cationic lipid.

This solution is completed with 153 µl of 20 mM HEPES pH 7.5 (adjusted with NaOH) in order to prepare a solution containing 5 mg/ml final of cationic lipid.

50 µg of plasmid DNA corresponding to 50 µl of a stock solution containing 1 mg/ml (in 10 mM Tris, 1 mM EDTA, pH 7.5) are diluted in 322 µl of 20 mM HEPES pH 7.5.

128 µl of pcTG42/DOPE are added to the 372 µl of the DNA solution in order to obtain 0.5 ml of complex containing 0.1 mg/ml of DNA and a charge ratio of 10. The suspension is mixed by aspiration/discharge using a pipette (10 times). The complexes are stored at +4° C.

Preparation of the Lipid-DNA Complexes by Suspending in a Detergent Solution

The amounts of lipids are calculated as described above for 0.5 ml final on the basis of the final DNA concentration (0.1 mg/ml for the in vitro tests), the desired charge ratio, the molar mass of cationic lipid and the number of positive charges on the cationic lipid chosen. The lipids are mixed together in a glass tube, sterilized with alcohol and with UV, in order to obtain a 2 mM solution of cationic lipid (see above). The solvents are evaporated off and the lipid film is taken up in a solution of n-octyl-β-D-glucopyranoside (octylglucoside, Sigma, 0 9882) in a cationic lipid/detergent ratio of 1/5 (mol:mol).

For example, from a 20 mM solution of octylglucoside in 20 mM HEPES pH 7.5, 250 µl are taken for 1 µmol of pcTG24 or pcTG42/DOPE, with which the film of lipid mixture is taken up. 50 µg of plasmid DNA corresponding to 50 µl of a stock solution containing 1 mg/ml (in 10 mM Tris, 1 mM EDTA, pH 7.5) are taken and added to 212.5 µl of 20 mM HEPES pH 7.5. 187.5 µl of the lipid suspension are added to the DNA by aspiration and discharge 10 times using a pipette in order to obtain the final suspension containing 0.1 mg/ml of DNA and a +/–charge ratio of 10. To remove the detergent, a dialysis of 3 times 4 hours at room temperature against 20 mM HEPES pH 7.5 is carried out in dialysis microbags (cut-off of 13.2 kD; Sartorius, Gottingen, Germany). The dialyzed DNA/lipid complexes are stored at +4° C. The preparation is carried out in a laminar-flow fume cupboard.

Preparation of the Lipid-DNA Complexes by Sonication-extrusion

The amounts of lipids are calculated as described above for 0.5 ml final based on the concentration of final DNA (0.1 mg/ml for the tests in vitro), the desired charge ratio, the molar mass of cationic lipid and the number of positive charges of the cationic lipid chosen. The lipids are mixed together in a glass tube, sterilized with alcohol and with UV, in order to obtain a 2 mM cationic lipid solution, as indicated above. The solvents are evaporated and the lipid film is taken up in 600 µl of 20 mM HEPES pH 7.5 at 4° C. for about 16 h. The suspension is sonicated in a sonication bath (Bransonic 221) up to visual homogeneity. The lipid suspension is extruded through two membranes with a pore diameter of 0.2 µm (Nucleopore, Costar, Cambridge, Mass., USA) and rinsed with 20 mM HEPES pH 7.5 (extruder from Lipex Biomembranes, Vancouver, Canada) at a maximum pressure of 50×105 Pa (50 bar). The lipid suspension is kept at room temperature for 1 hour. 450 µl of the lipid suspension are added to 50 µl of a stock solution of plasmid DNA (1 mg/ml) and mixed by aspiration/discharging 10 times using a pipette. The lipid/DNA complexes are stored at +4° C. The preparations are carried out under a laminar flow fume cupboard.

Protocol for Evaluating the Complexing of the DNA by the Lipids

A 1% (w:v) agarose gel is prepared in a TAE buffer (TAE : Tris 4.86 g/l+sodium acetate 0.68 g/l+EDTA 0.336 g/l pH 7.8). If necessary, the sample is diluted in TAE and then the sample buffer (0.083% bromophenol blue, 0.083% cyanol xylene FF, 10% glycerol in water) is added so as to have 50 ng of DNA/µl. The sample is briefly vortexed and left for 30 min at room temperature. As a control, the non-complexed plasmid prepared at the same concentration is used. 10 µl (500 ng of DNA) are deposited on the gel and the migration is carried out at 60 mV for 3 hours. The gel is developed in TAE containing 0.006% (v:v) of ethidium bromide at 10 mg/ml for at least 30 min. Next, the gel is rinsed in TAE and analyzed under UV.

Protocol for Measuring the Size of the Particles by Quasi-elastic Light Scattering The analyses are carried out on a Coulter N4Plus (Coultronics France S.A., Margency, France) at 25° C. after equilibration of the sample for 20 min. An aliquot of the sample is aspirated and discharged several times before being pipetted. The sample is diluted in the measuring tank and homogenized. The measurement of the light diffracted at 90° is carried out for 180 sec after a 180 sec wait. The range used goes from 3 nm to 10,000 nm using 31 bins. To be valid, the sample should give between 50,000 and 1,000,000 counts/sec.

Physicochemical Characteristics

The three methods of formulation "injection of ethanol", "dialysis of detergent" and "sonication/extrusion" are applied to the cationic lipids according to the invention with or without equimolecular amounts of DOPE at charge ratios of about 10, or 5. The formulations are considered to be appropriate for selection for the reproducibility studies when the DNA is completely complexed (no migration in the agarose gel) and when the complexes have particle diameters, determined by quasi-elastic light scattering, which allow an in vivo administration.

In general, all the DNA/lipid complexes tested (based on pcTG24, pcTG42, pcTG52, pcTG54 or pcTG55) complex the DNA completely, in the presence or absence of DOPE.

Moreover, formulation by suspension in ethanol proves to be advantageous for generating small complexes (less than 500 nm), which are particularly appropriate for the purpose of an in vivo administration, and does so with all the lipids tested.

As examples, complexes with a diameter of less than or about 200 nm are obtained in the following cases:
DNA/pcTG24/DOPE for a charge ratio R=5
DNA/pcTG42 for a charge ratio R=10
DNA/pcTG42/DOPE for a charge ratio R=10 or 5
DNA/pcTG52/DOPE for a charge ratio R=5 or 10
DNA/pcTG54/DOPE for a charge ratio R=5 or 10
DNA/pcTG55 for a charge ratio R=10

The complexes based on pcTG42 lipid which are produced by the various formulation methods were evaluated. Complexes less than or close to 200 nm in size are obtained for the DNA/pcTG42 compositions at a charge ratio R=10, prepared by suspension in a solution of n-octyl-β-D-glucopyranoside and DNA/pcTG42/DOPE at a charge ratio R=10 obtained by sonication in vitro transfection of Satellite Cells The reporter plasmid pTG11033 is used to evaluate the transfecting efficacy of the compounds of the invention. It includes the CMV promoter which directs the expression of the luciferase gene.

Cultures of dog muscles and human muscles are carried out in a HamF 14 medium (Life Technologies) supplemented with 10% fetal calf serum (FCS, Hyclone, Logan, Utah), 10 μg/ml of insulin (Sigma), 10 ng/ml of EGF (Sigma) and of basic FGF (Pepro Tech Inc., Rocky Hill, N.J.), 2 mM of glutamine (bioMérieux) and 40 μg/ml of gentamycin (Schering Plough).

The cells are inoculated 24 h to 48 h before the transfection, into a 96-well cell dish at a rate of 5×103 to 104 cells per well, at about 30% confluence, and kept at 37° C. in an atmosphere containing 5% $CO_2$ and 95% air.

The transfections are carried out with mixtures of variable amounts of lipids and of plasmid DNA in order to determine the ionic charge ratios and the optimum DNA concentrations per well.

The complexes used are prepared 24 h to 48 h before the transfection and diluted in the HamF 14 medium containing 40 pg/ml of gentamycin and 2 mM of glutamine in the presence or absence of 10% FCS.

After removing the culture medium, 100 μl of transfection mixtures are transferred into each of the wells.

After 4 hours at 37° C., all of the transfection media are then adjusted to 10% FCS or (FCS +plasma), 10 μg/ml of insulin (Sigma), 10 ng/ml of EGF (Sigma) and of basic FGF (Pepro Tech Inc., Rocky Hill, N.J.), of 2 mM glutamine (BioMérieux) and 40 μg/ml of gentamycin (Schering Plough) for a final volume of 250 μl. The cultures are incubated for 48 h and the cells are then recovered and tested for their capacity to express the luciferase gene.

Transfection of A549 Cells

The A549 cells (epithelial cells derived from human pulmonary carcinoma) are cultured in Dulbecco's modified Eagle's medium (DMEM) containing 10% fetal calf serum (Gibco BRL) 24 hours before the start of the transfection in 96-well plates (2×104 cells per well) in a humid atmosphere at 37° C. and 5% $CO_2$/95% air. For the transfection in the absence of serum, the medium is removed and replaced with serum-free medium. In another microplate, the following suspensions of lipid/DNA complexes are prepared (lipid/DNA complexes at 0.1 mg/ml of DNA and at the indicated charge ratio): 44 μl (4.4 μg DNA), 22 μl (2.2 μg DNA), 5.5 μl (0.55 μg DNA) of stock solution in the first 3 wells, and 11 μl (0.11 μg DNA) of the stock solution diluted 10-fold in the next well. The volume is adjusted to 110 μl with DMEM and 100 μl are transferred over the A549 cells. The incubation is carried out with 4, 2, 0.5 and 0.1 μg of DNA per well for 4 hours. 50 μl of DMEM +30% fetal calf serum are added 4 hours after the start of transfection. Finally, 100 μl of DMEM +10% FCS are added 24 hours after the start of transfection. The transfections in the presence of 10% fetal calf serum are carried out in an identical manner except that the transfection occurs in medium with serum.

Analysis of the Transfection 48 h after the transfection, the medium is removed and the cells are washed with 100 μl of PBS phosphate solution and lyzed with 50 μl of lysis buffer (Promega). The lyzates are frozen at −80° C. until the luciferase activity is measured. The latter is carried out on 20 μl of mixture for one minute using the "Luciferase" determination system (Promega) (LB96P Berthold luminometer) in 96-well plates in kinetic mode.

Results of the Transfection Tests

The preparations based on pcTG24 and pcTG42 in the presence or absence of DOPE were evaluated in in vitro transfection using the A549 cells and the dog primary satellite cells. The relative light units (RLU) per well are evaluated by varying the amount of DNA per well (4, 2, 0.5 and 0.1 μg) and the experimental conditions (transfection in the presence or absence of serum).

The transfection of the A549 pulmonary cells with the pTG11033/pcTG24 complexes allows high levels of expression of the luciferase gene; in particular at a low concentration of DNA (0.1 μg) and in the absence of serum. The presence of DOPE in the preparations increases the transfecting activity, allowing larger amounts of DNA in the complexes (0.1 to 0.5 μg) and of the serum to be included during the transfection.

Similarly, the pTG11033/pcTG42 complexes are capable of transfecting the A549 cells. The expression of the luciferase gene is highest at a low concentration of DNA (0.1 μg). Little or no significant difference dependent on the transfection experimental conditions (with or without serum) is observed. The transfecting efficacy is increased when the preparation contains DOPE. This effect is even more beneficial when the transfection is carried out in the presence of serum.

The DNA/pcTG42/DOPE complexes are most particularly suitable for transfecting muscle cells. High levels of luciferase expression are obtained at a low DNA concentration (0.1 μg).

EXAMPLE 13

Preparation of cis and trans Isomers of Cationic Lipids Centered on a Piperazine or Homopiperazine Unit

Diamide ANI 181

A solution of 2-bromo-N,N-dioctylacetamide (1.05 g; 2.90 mmol) in a mixture of THF and acetonitrile (1/1; v/v; 5 ml) is added slowly to a solution of piperazine (0.125 g; 1.45 mmol) and diisopropylethylamine (0.187 g; 2.90 mmol) in acetonitrile (20 ml). The yellowish heterogeneous mixture is stirred for 4 h at 0° C. and then diluted with ether and washed with a saturated aqueous sodium carbonate solution. The organic phase is dried over sodium sulfate, concentrated under reduced pressure and purified by chromatography on a column of silica gel (eluent: 5/95 methanol/dichloromethane) to give the diamide ANI 181 (0.852 g; 91%) in the form of a colorless oil.

$^1$H NMR (200 MHz, CDCl$_3$): δ3.27 (t, J=7.4 Hz, 8H, —CH$_2$)$_2$N—C(O)—); 3.14 (s, 4H, N—CH$_2$—C(O)—); 2.55 (s, 8H, —N(CH$_2$—CH$_2$)$_2$N—); 1.52 (m, 8H, —CH$_2$—CH$_2$)$_2$N—C(O)—); 1.28 and 1.26 (2s, 40H, —CH$_2$—); 0.89 and 0.87 (2t, J=6.6 Hz, 12H, Me-).

Diamide ANII 21

The same procedure as for diamide ANI 181 allows the preparation of the diamide ANII 21 (545 mg; 92%) in the form of a colorless oil, starting with 2-bromo-N,N-dioctylacetamide (650 mg; 1.79 mmol) and homopiperazine (90 mg; 0.89 mmol) in the presence of diisopropylethylamine (232 mg; 1.79 mmol).

$^1$H NMR (200 MHz, CDCl$_3$): δ3.30 (s, 4H, N—CH$_2$—C(O)—), 3.30 and 3.26 (2t, J=8 Hz, 8H, —CH$_2$)$_2$N—C(O)—); 2.76 (t and s, J=5.5 Hz, 8H, N—CH$_2$—CH$_2$—CH$_2$—N and N—CH$_2$—CH$_2$—N); 1.82 (quint., 2H, J=5.5 Hz, N—CH$_2$—CH$_2$—CH$_2$—N; 1.51 (m, 8H, —CH$_2$—CH$_2$)$_2$N—C(O)—); 1.27 and 1.25 (2s, 40H, —CH$_2$—); 0.88 and 0.86 (2t, J=6.7 HZ, 12H, Me-).

Oleyl 2-bromoacetate

A solution of bromoacetyl bromide (0.49 ml; 5.65 mmol) in tetrahydrofuran (12 ml) is added, at 0° C., to a mixture of oleyl alcohol (1.00 ml; 3.77 mmol) and diisopropylethylamine (0.88 g; 5.65 mmol) in tetrahydrofuran (38 ml). The mixture is stirred for 2 h at 0° C. and then for 1 h at room temperature; it is then washed with 1N hydrochloric acid solution (20 ml) which is extracted with ether (50 ml). The combined organic phases are washed with saturated sodium carbonate solution (20 ml), dried over sodium sulfate, concentrated under reduced pressure and purified by chromatography on a column of silica gel (eluent: 99/1 hexane/ether) to give oleyl 2-bromoacetate (1.31 g; 89%) in the form of a colorless oil.

$^1$H NMR (200 MHz, CDCl$_3$): δ5.34 (m, 2H, —CH=); 4.16 (t, J=6.6 Hz, 2H, —CH$_2$—O—C(O)—); 3.82 (s, 2H, BrCH$_2$—C(O)—); 2.00 (m, 4H, —CH$_2$—CH=); 1.67 (m, 4H, —CH$_2$—CH—)$_2$O—C(O)—); 1.30 and 1.26 (2s, 22H, —CH$_2$—); 0.87 (t, J=6.3 Hz, 3H, Me-).

Isomeric Cationic Lipids ANII 16 F1 and ANII 16 F2

Iodomethane (1 ml) is added to a solution of diamide ANI 181 (316 mg, 0.49 mmol) in acetonitrile (5 ml) and the mixture is refluxed for 4 h. After cooling, the solution is concentrated under reduced pressure and the yellowish crude reaction product is purified by chromatography on a column of silica gel (eluent: 60/35/5 ether/dichloromethane/methanol and then 85/15 dichloromethane/methanol) to give two isomeric cationic lipids ANII 16 F1 (142 mg; 31%) and ANII 16 F2 (245 mg; 54%).

ANII 16 F1: m.p.=148° C.

$^1$H NMR (200 MHz, CDCl$_3$—CF$_3$CO$_2$D): δ5.09 (broad s, 4H, N$^+$—CH$_2$—C(O)—); 4.79 and 4.50 (broad 2d, J=11 Hz, 8H, —CH$_2$—N$^+$); 3.85 (s, 6H, Me—N$^+$); 3.31 (m, 8H, —CH$_2$)$_2$N—C(O)—); 1.58 (m, 8H, —CH$_2$—CH2)$_2$N—C(O)—); 1.27 (broad s, 40H, —CH$_2$—); 0.88 (t, J=6.3 Hz, 12H, Me-).

ANII 16 F2: m.p.=143° C. $^1$H NMR (200 MHz, CDCl$_3$—CF$_3$CO$_2$D): δ5.21 (broad s, 4H, N$^+$—CH$_2$—C(O)—); 5.00–4.80 and 4.60–4.40 (2m, 8H, —CH$_2$—N$^+$); 3.82 (s, 6H, Me—N$^+$); 3.33 (m, 8H, —CH$_2$)$_2$N—C(O)—); 1.60 (m, 8H, —CH$_2$—CH$_2$)$_2$N—C(O)—); 1.27 (broad s, 40H, —CH$_2$—); 0.88 (t, J=6.3 Hz, 12H, Me-).

Isomeric Cationic Lipids ANII 22 F1 and ANII 22 F2

The same procedure as for the cationic lipids ANII 16 allows the preparation of the cationic lipids ANII 22 F1 (168 mg; 29%) and ANII 22 F2 (255 mg; 45%), starting with the diamide ANII 21 (400 mg; 0.603 mmol) and iodomethane (1 ml).

ANII 22 F1: m.p.=144–145° C.

$^1$H NMR (200 MHz, CDCl$_3$—CF$_3$CO$_2$D): δ5.05–4.10 (m, 12H, N$^+$—CH$_2$—C(O)— and —CH$_2$—N$^+$); 3.62 (s, 6H, Me—N$^+$); 3.29 (m, 8H, —CH$_2$)$_2$N—C(O)—); 2.78 (m, 2H, —N$^+$13 CH$_2$—CH$_2$—CH$_2$—N$^{+—}$)$^,$ 1.57 (m, 8H, —CH$_2$—CH$_2$)$_2$—N—C(O)—); 1.28 (broad s, 40H, —CH$_2$—); 0.88 (t, J=6.3 Hz, 12H, Me-).

ANII 22 F2: 122–124° C.

$^1$H NMR (200 MHz, CDCl$_3$—CF$_3$CO$_2$D): δ5.10–4.25 (m, 12H, N$^+$—CH$_2$—C(O)— and —CH$_2$—N$^+$); 3.65 (s, 6H, Me—N$^+$); 3.30 (m, 8H, —CH$_2$)$_2$N—C(O)—); 2.75 (m, 2H, —N$^+$—CH$_2$—CH$_2$—CH$_2$—N$^{+—}$)$^,$ 1.58 (m, 8H, —CH$_2$—CH$_2$)$_2$N—C(O)—); 1.27 (broad s, 40H, —CH$_2$—); 0.88 (t, J=6.4 Hz, 12H, Me-).

Isomeric Cationic Lipids ANII 39 F1 and ANII 39 F2

A solution of N,N'-dimethyl-1,4-piperazine (26 mg; 0.226 mmol) and oleyl 2-bromoacetate (220 mg; 0.565 mmol) in acetonitrile (5 ml) is refluxed for 16 h. The solution is concentrated under reduced pressure and the residue is purified by chromatography on a column of silica gel (eluent: 40/45/15 and then 40/40/20 ethyl acetate/dichloromethane/methanol) to give the two isomeric cationic lipids ANII 39 F1 (75 mg; 37%) and ANII 39 F2 (40 mg; 20%).

ANII 39 F1: m.p.=173–175° C.

$^1$H NMR (200 MHz, CDCl$_3$—CF$_3$CO$_2$D): δ5.36 (m, 4H, —CH=); 4.79 (broad s, 4H, N$^+$—CH$_2$—C(O)—); 4.65 and 4.35 (broad 2d, J=11 Hz, 8H, —CH$_2$—N$^+$); 4.26 (t, J=6.8 Hz, 4H, —CH$_2$—O—C(O)—); 3.74 (s, 6H, Me—N$^+$); 2.02 (m, 8H, CH$_2$—CH=); 1.68 (m, 4H, —CH$_2$—CH$_2$—O—C(O)—); 1.29 (broad s, 40H, —CH$_2$—); 0.88 (t, J=6.4 Hz, 6H, Me-)

ANII 39 F2: m.p.=163–165° C.

$^1$H NMR (200 MHz, CDCl$_3$—CF$_3$CO$_2$D): δ5.36 (m, 4H, —CH=); 4.84 (s, 4H, N$^+$—CH$_2$—C(O)—); 4.70–4.30 (m, 8H, —CH$_2$—N$^+$); 4.25 (t, J=6.9 Hz, 4H, —CH$_2$—O—C(O)—); 3.75 (s, 6H, Me—N$^+$); 2.02 (m, 8H, —CH$_2$—CH=); 1.67 (m, 4H, —CH$_2$—CH$_2$—O—C(O)—); 1.29 and 1.27 (2s, 40H, —CH$_2$—); 0.88 (t, J=6.4 Hz, 6H, Me-)

Diamide ANII 151

The same procedure as for the diamide ANI 181 allows the preparation of the diamide ANII 151 (197 mg; 84%) in the form of a colorless oil, starting with 2-bromo-N,N-di(tetradecyl)acetamide (310 mg; 0.584 mmol) and homopiperazine (23 mg; 0.23 mmol) in the presence of diisopropylethylamine (60 mg; 0.47 mmol).

$^1$H NMR (200 MHz, CDCl$_3$) δ3.30 (s, 4H, N—CH$_2$—C(O)—), 3.28 (m, 8H, —CH$_2$)$_2$N—C(O)—); 2.77 (m, 8H, N—CH$_2$—CH$_2$—CH$_2$—N and N—CH$_2$—CH$_2$—N); 1.82 (m, 2H, N—CH$_2$—CH$_2$—CH$_2$—N); 1.53 (m, 8H, —CH$_2$—CH$_2$)$_2$N—C(O)—); 1.26 and 1.25 (2s, 88H, —CH$_2$—); 0.88 (t, J=6.4 Hz, 12H, Me).

Isomeric Cationic Lipids ANII 152 F1 and ANII 152 F2

The same procedure as for the cationic lipids ANII 16 allows the preparation of the cationic lipids ANII 152 F1 (58 mg; 30%) and ANII 152 F2 (84 mg; 44%), starting with the diamide ANII 151 (150 mg; 0.150 mmol) and iodomethane (1 ml).

ANII 152 F1: m.p.=130° C.

$^1$H NMR (200 MHz, CDCl$_3$—CF$_3$CO$_2$D): δ5.15–4.30 (m, 12H, N$^+$—CH$_2$—C(O)— and —CH$_2$—N$^+$); 3.70 (broad s, 6H, Me—N$^+$); 3.30 (m, 8H, —CH$_2$)$_2$N—C(O)—); 2.81 (m, 2H, —N$^+$—CH$_2$—CH$_2$—CH$_2$—N$^+$—), 1.59 (m, 8H, —CH$_2$—CH$_2$)$_2$N—C(O)—); 1.26 (broad s, 88H, —CH$_2$—); 0.88 (t, J 6.4 Hz, 12H, Me-).

ANII 152 F2: m.p.=118° C. 1H NMR (200 MHz, CDCl$_3$—CF$_3$CO$_2$D): δ5.20–4.20 (m, 12H, N$^+$—CH$_2$—C(O)— and —CH$_2$—N$^+$); 3.67 (broad s, 6H, Me—N$^+$); 3.30 (m, 8H, —CH$_2$)$_2$N—C(O)—); 2.86 (m, 2H, —N$^+$—CH$_2$—CH$_2$—CH$_2$—N$^+$—), 1.57 (m, 8H, —CH$_2$—CH$_2$)$_2$N—C(O)—); 1.25 (broad s, 88H, —CH2—); 0.87 (t, J=6.4 Hz, 12H, Me-).

Isomeric Cationic Lipids ANII 150 F1 and ANII 150 F2

The same procedure as for the cationic lipids ANII 39 allows the preparation of the cationic lipids ANII 150 F1 (61 mg; 31%) and ANII 150 F2 (37 mg; 19%), starting with 2-bromo-N,N-di(tetradecyl)acetamide (220 mg; 0.415 mmol) and N,N'-dimethyl-1,4-piperazine (19 mg; 0.17 mmol).

ANII 150 F1: m.p.=1110° C.

$^1$H NMR (200 MHz, CDCl$_3$—CF$_3$CO2D): δ4.88 (broad s, 4H, N$^+$—CH$_2$—C(O)—); 4.70 and 4.39 (2m, 8H, —CH$_2$—N$^+$); 3.73 (s, 6H, Me—N$^+$); 3.28 (m, 8H, —CH$_2$)$_2$N—C(O)—); 1.56 (m, 8H, —CH$_2$—CH$_2$)$_2$N—C(O)—); 1.26 (broad s, 88H, —CH$_2$—); 0.88 (t, J=6.4 Hz, 12H, Me-).

ANII 150 F2: m.p.=100–1020° C.

$^1$H NMR (200 MHz, CDCl$_3$—CF$_3$CO$_2$D): δ5.02 (broad s, 4H, N$^+$—CH$_2$—C(O)—); 4.90–4.65 and 4.50–4.25 (2m, 8H, —CH$_2$—N$^+$); 3.71 (s, 6H, Me—N$^+$); 3.29 (m, 8H, —CH$_2$)$_2$N—C(O)—); 1.56 (m, 8H, —CH$_2$—CH$_2$)$_2$N—C(O)—); 1.25 (broad s, 88H, —CH$_2$—); 0.88 (t, J=6.4 Hz, 12H, Me-).

Isomeric Cationic Lipids ANII 157 F1 and ANII 157 F2

The same procedure as for the cationic lipids ANII 39 allows the preparation of the cationic lipids ANII 157 F1 (65 mg; 33%) and ANII 157 F2 (22 mg; 11%), starting with 2-bromo-N,N-dioleylacetamide (136 mg; 0.211 mmol) and N,N'-dimethyl-1,4-piperazine (16 mg; 0.14 mmol).

ANII 157 F1:

$^1$H NMR (200 MHz, CDCl$_3$): δ5.48–5.30 (m, 12H, —CH= and N+—CH$_2$—C(O—); 4.95 and 4.74 (2m, 8H, —CH$_2$—N$^+$); 4.03 (broad s, 6H, Me—N+); 3.29 (m, 8H, —CH$_2$)$_2$N—C(O)—); 2.01 (m, 16H, —CH$_2$—CH=); 1.53 (m, 8H, —CH$_2$—CH2—N—C(O)—); 1.28 and 1.27 (broad 2s, 88H, —CH$_2$—); 0.88 (t, J=6.4 Hz, 12H, Me-)

ANII 157 F2:

$^1$H NMR (200 MHz, CDCl$_3$): δ5.45 (m, 4H, N$^+$—CH$_2$—C(O)—) 5.34 (m, 8H, —CH=); 5.09 and 4.66 (2m, 8H, —CH$_2$—N$^+$); 3.99 (broad s, 6H, Me—N$^+$); 3.25 (m, 8H, —CH$_2$—N—C(O)—); 2.00 (m, 16H, —CH$_2$—CH=); 1.52 (m, 8H, —CH$_2$—CH$_2$—N—C(O)—); 1.27 (broad s, 88H, —CH$_2$—); 0.87 (t, J=6.4 Hz, 12H, Me-).

EXAMPLE 14

Analysis of Novel Lipid Complexes 1. Formulation of the DNA/cationic Lipid Complexes by Mixing with a Solvent The required amounts of each of the cationic lipids are measured out and dissolved in a CHCl$_3$/MeOH mixture (v/v: 1/1). If necessary, an equimolar amount of DOPE (Avanti Polar Lipids, Alabaster, Ala.) is added using an evaporation (Labconco Rapidvap Model 79000; UniEquip) at 450° C., 40 rpm for 45 minutes under vacuum. The lipid film obtained is redissolved in order to obtain a total lipid concentration of 50 mg/ml in an ethanol/DMSO mixture (v/v : 1/1). The lipid suspension is then rapidly mixed with 20 mM HEPES, pH 7.5 in order to obtain a final lipid concentration of 5 mg/ml. The formation of the complexes with the purified plasmid DNA, a preparation at 1 mg/ml of plasmid in TE (10 mM TRIS, 1 mM EDTA, pH 7.5) is diluted with 20 mM HEPES, pH 7.5 in order to obtain the desired concentration and is supplemented with lipid suspension as described previously in order to reach a DNA concentration of 0.1 mg/ml with the desired charge ratio. Moreover, in order to obtain small complexes and in order to avoid the problems of precipitation, it is important to mix the compounds rapidly by aspiration/propulsion using pipettes. All of the preparations are stored at 4 ° C. before being used.

2. Formulation of the DNA/cationic Lipid Complexes by Mixing with a Detergent and Dialysis The amounts of lipid are calculated in order to obtain DNA/lipid complexes containing 0.1 mg of DNA/ml and with the desired charge ratio. After drying the lipid solution (2 mM), the lipid film is taken up in a 20 mM pH 7.5 HEPES solution containing 20 mM n-octyl-β-D-glucopyranoside at a detergent/lipid weight ratio of 5/1. The plasmid DNA solution is prepared using a 1 mg/ml stock solution. The lipid suspension is added to the DNA by rapid and repeated pipetting in order to obtain a nucleic acid concentration of 0.1 mg/ml and a charge ratio of 10. The detergent is removed by a step of dialysis against 20 Mm hepes [sic], pH 7.5 for 3 to 4 hours (cut-off: 13 kD; Sartorius).

3. in vitro Transfection with the DNA/cationic Lipid Complexes

The A549 cells (human epithelial pulmonary cancer cells) are cultured according to the standard conditions in microtitration plates for 24 hours. The complexes are prepared according to one of the techniques described above. A series of cascade dilutions of the complexes (2 to 0.01 μg of complexed plasmid) is prepared. These dilutions are added (225 μl) to the cultured cells. 4 hours after the start of the incubation, 25 μl of fetal calf serum are optionally added.

The transfection is stopped after 48 hours. The culture medium is removed with 100 μl of PBS and then lyzed with 50% 1 [sic] of lysis buffer (Promega). Up to the time of measurement of the luciferase activity, the lyzed cells are stored at −80° C. The luciferase activity is measured on a 20 μl alicote [sic] using a Berthold LB96P luminometer. A calibration standard range is prepared in parallel in order to correlate the activity measured, in RLU, with the amount expressed in fg of expressed luciferase. The protein measurement is carried out according to the BCA standard procedure as proposed by the supplier (Pierce).

4. Results

Figure 2:
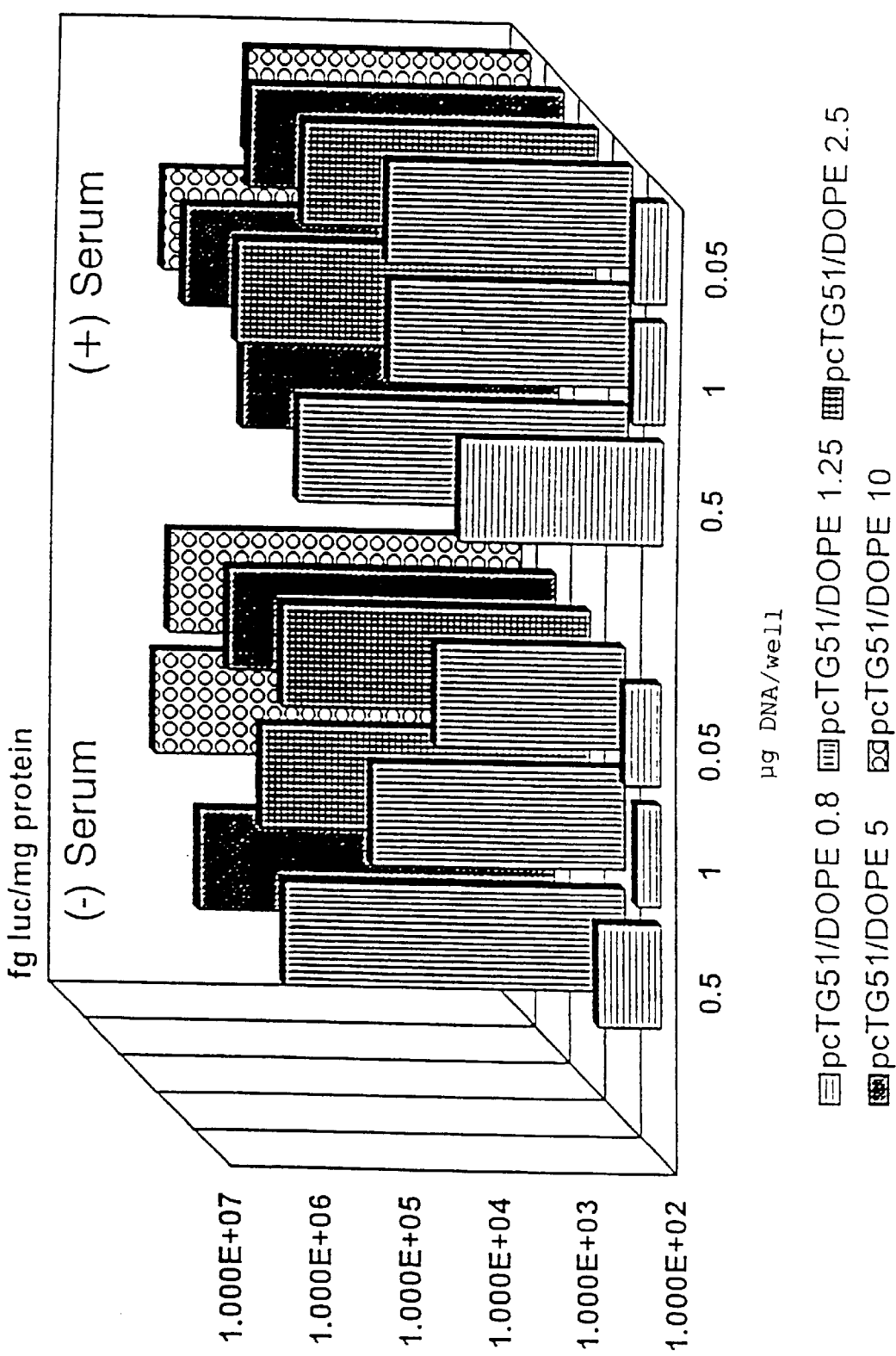
Figure 3:
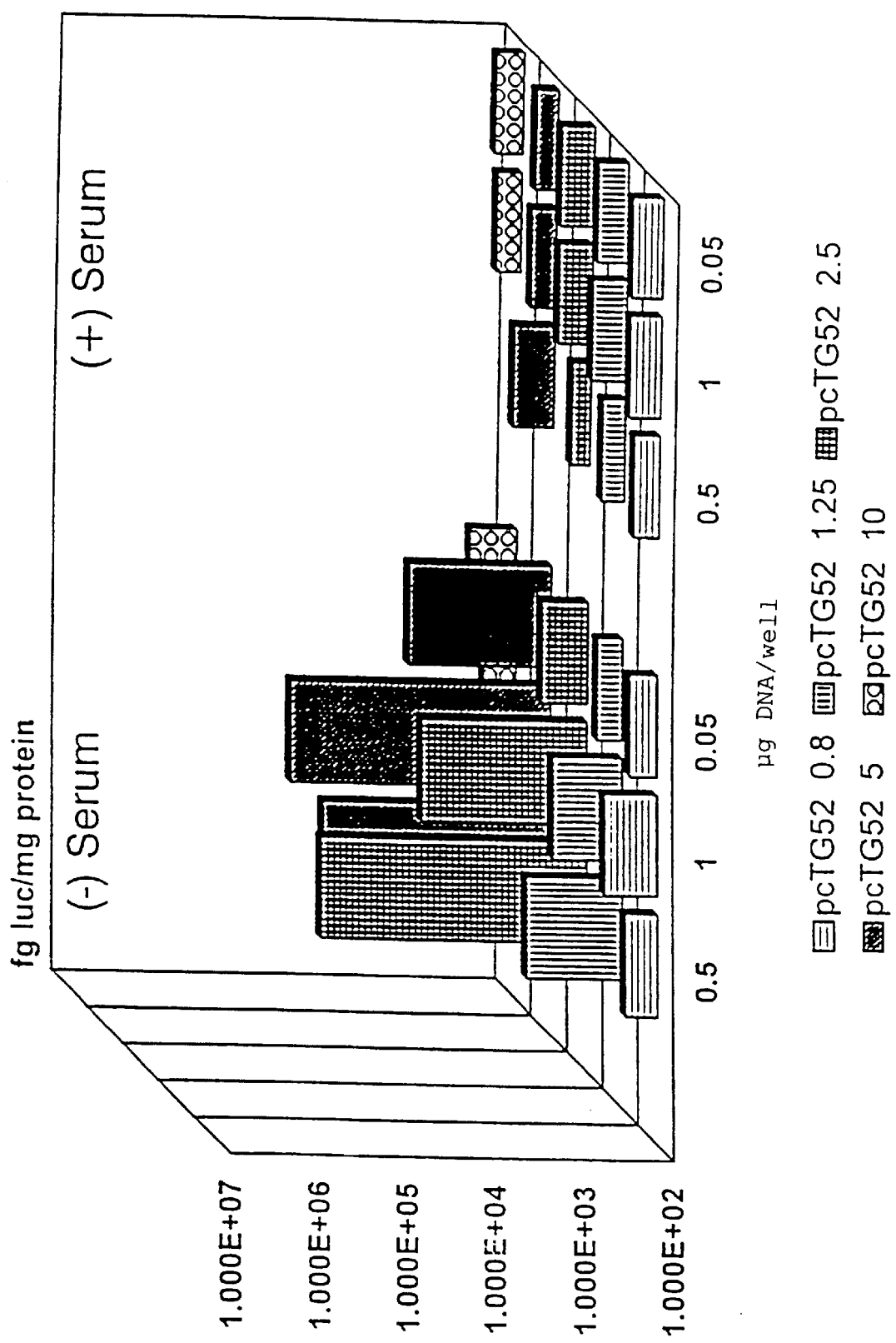
Figure 4:
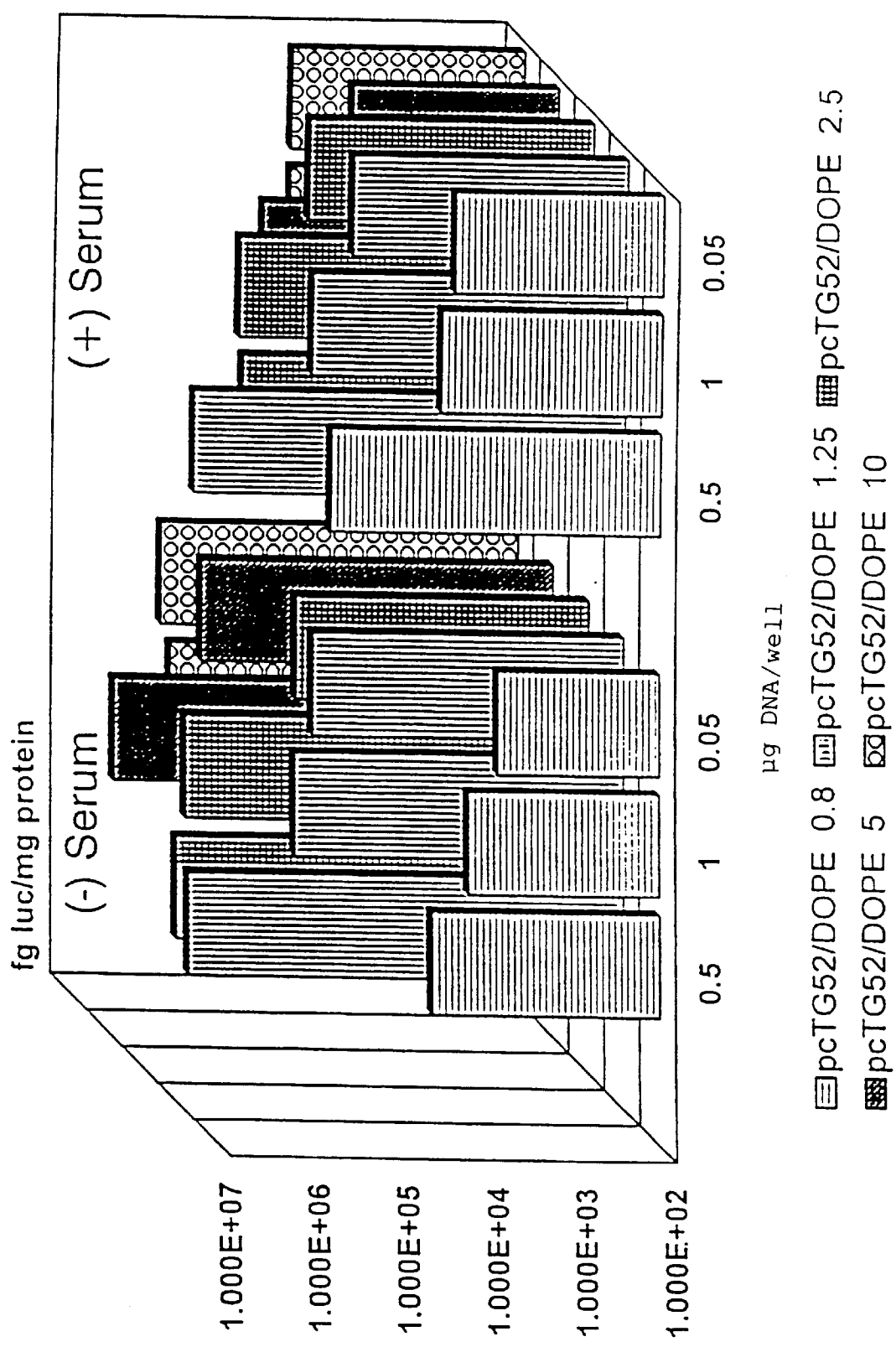
Figure 5:
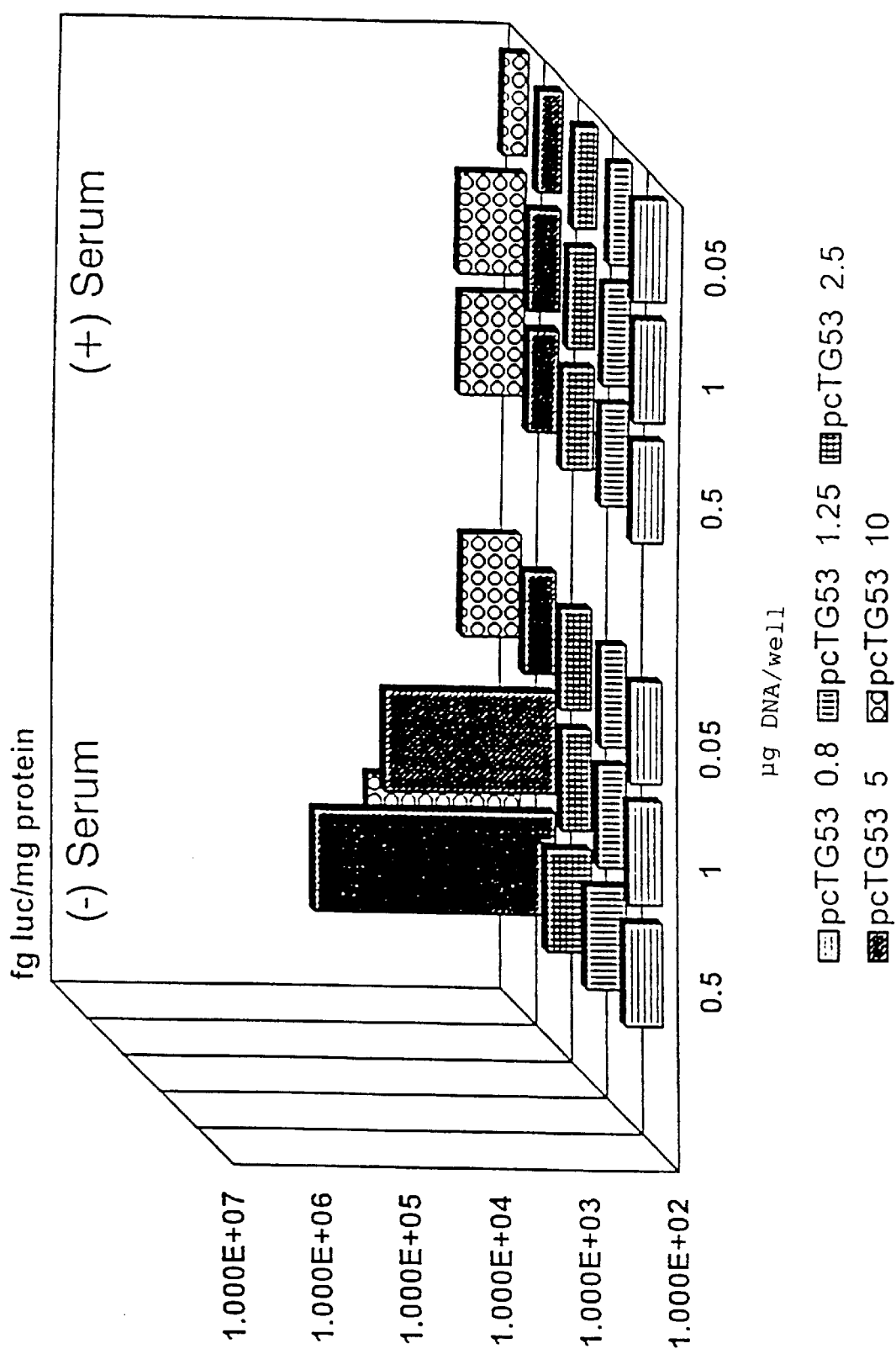
Figure 6:
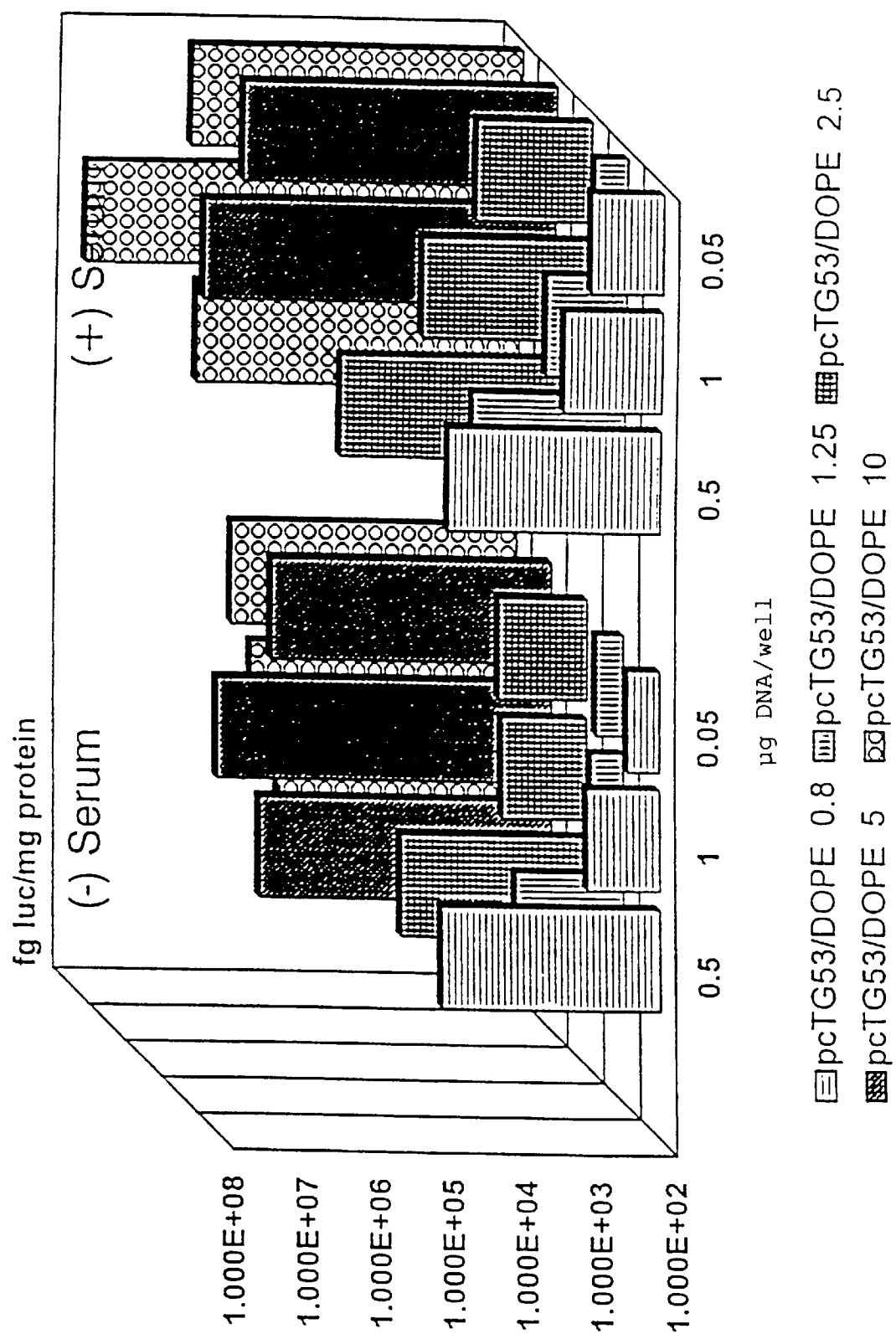
Figure 7:
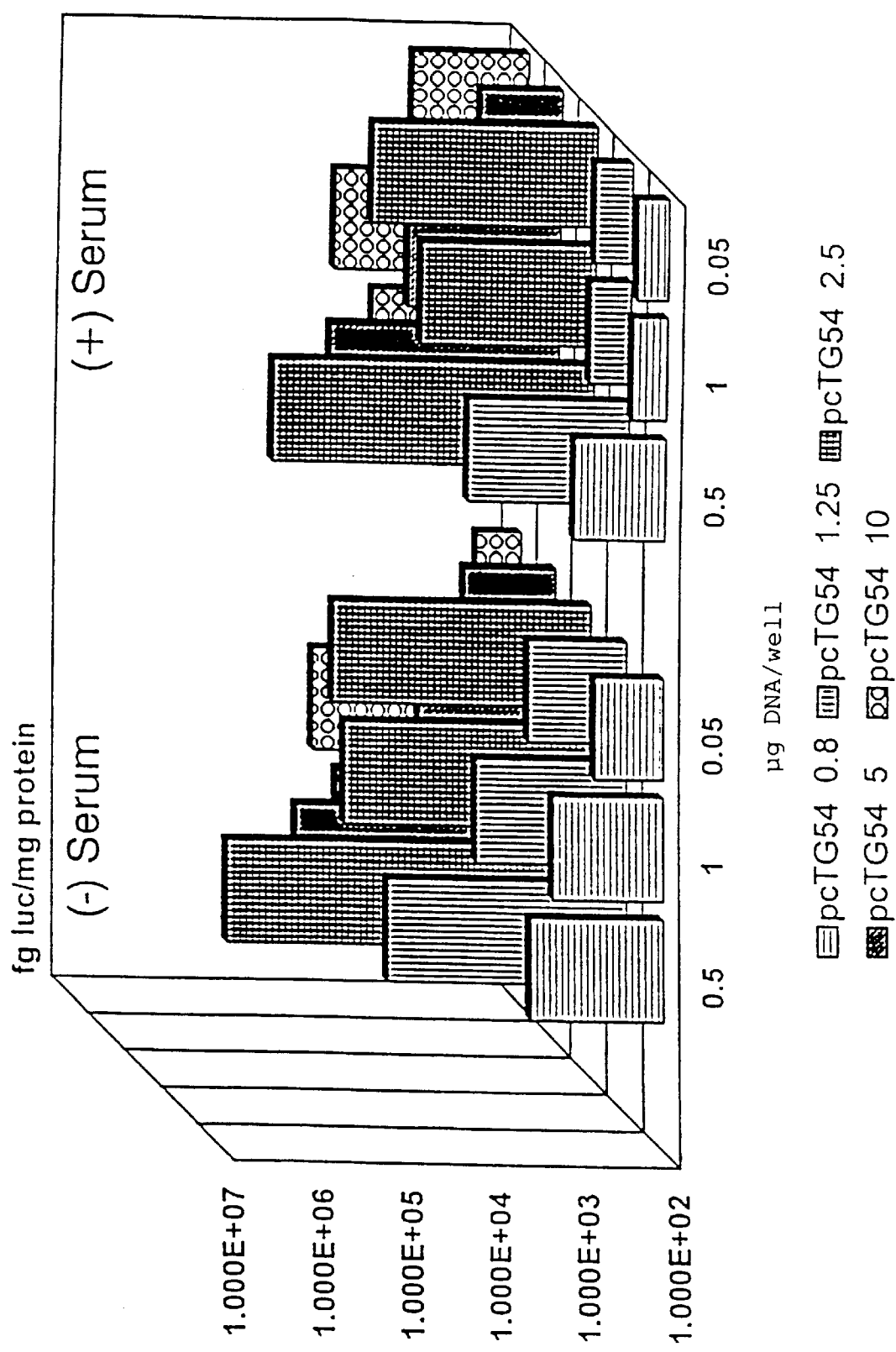
Figure 8:
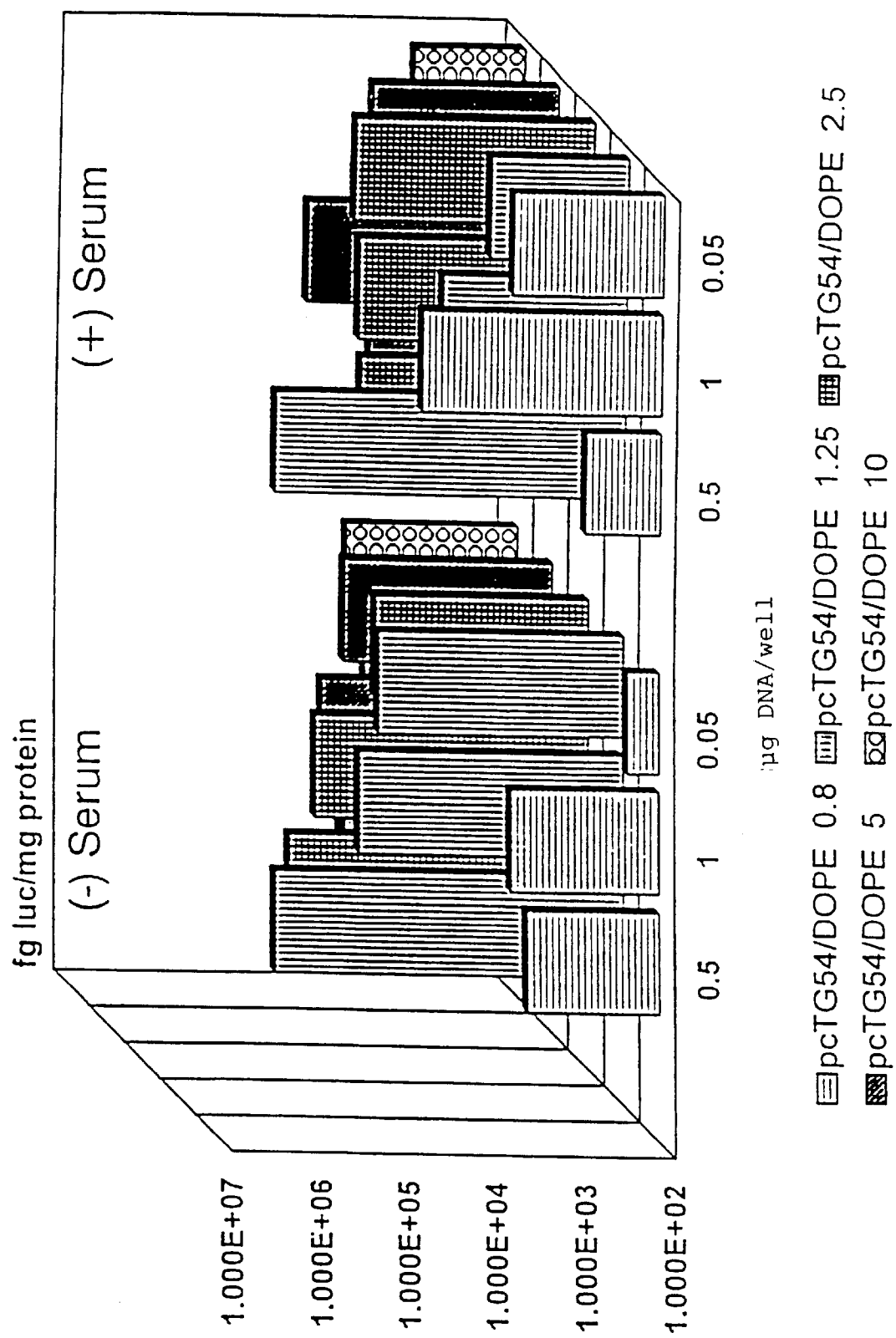
Figure 9:
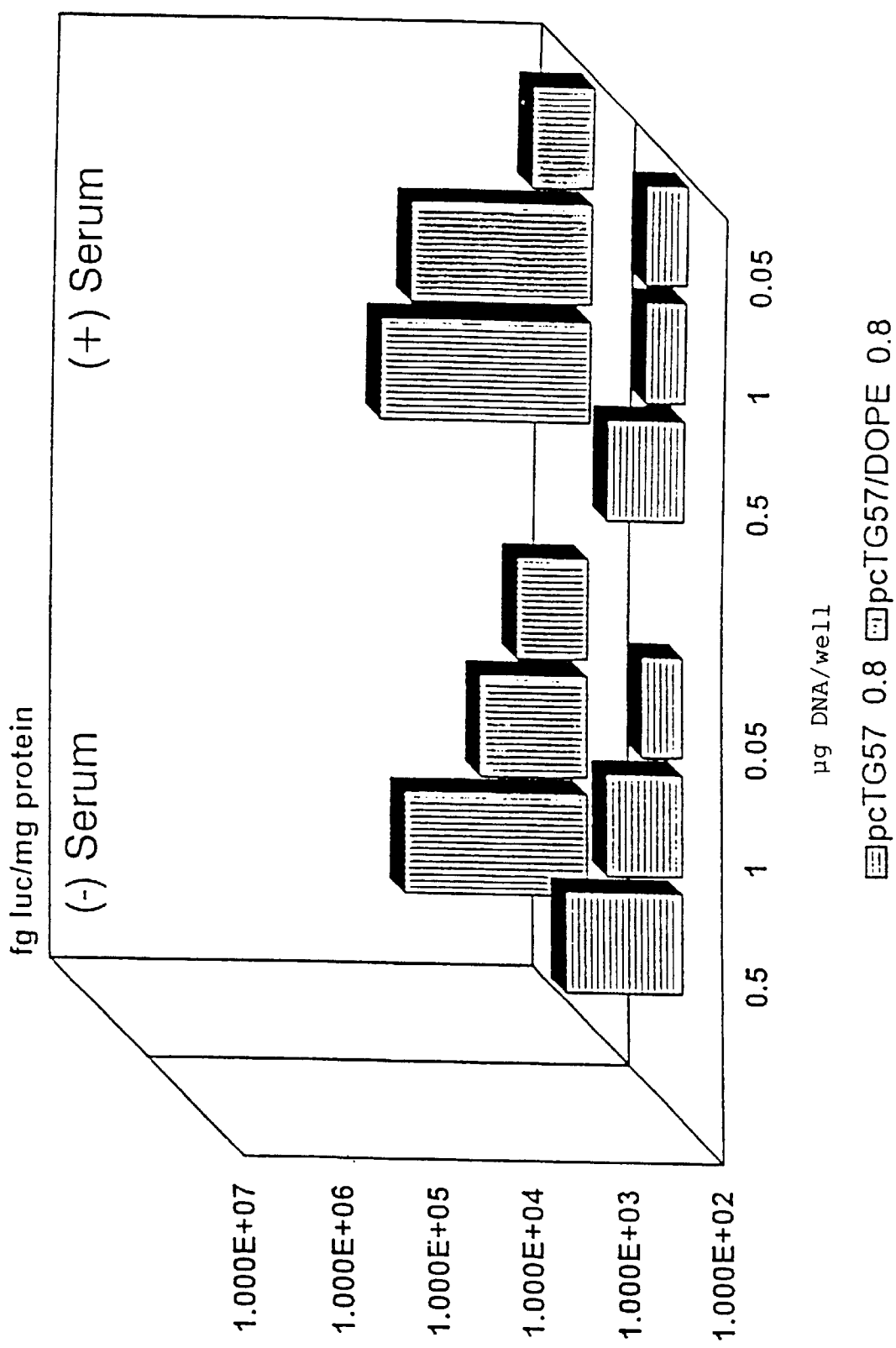
Figure 10:
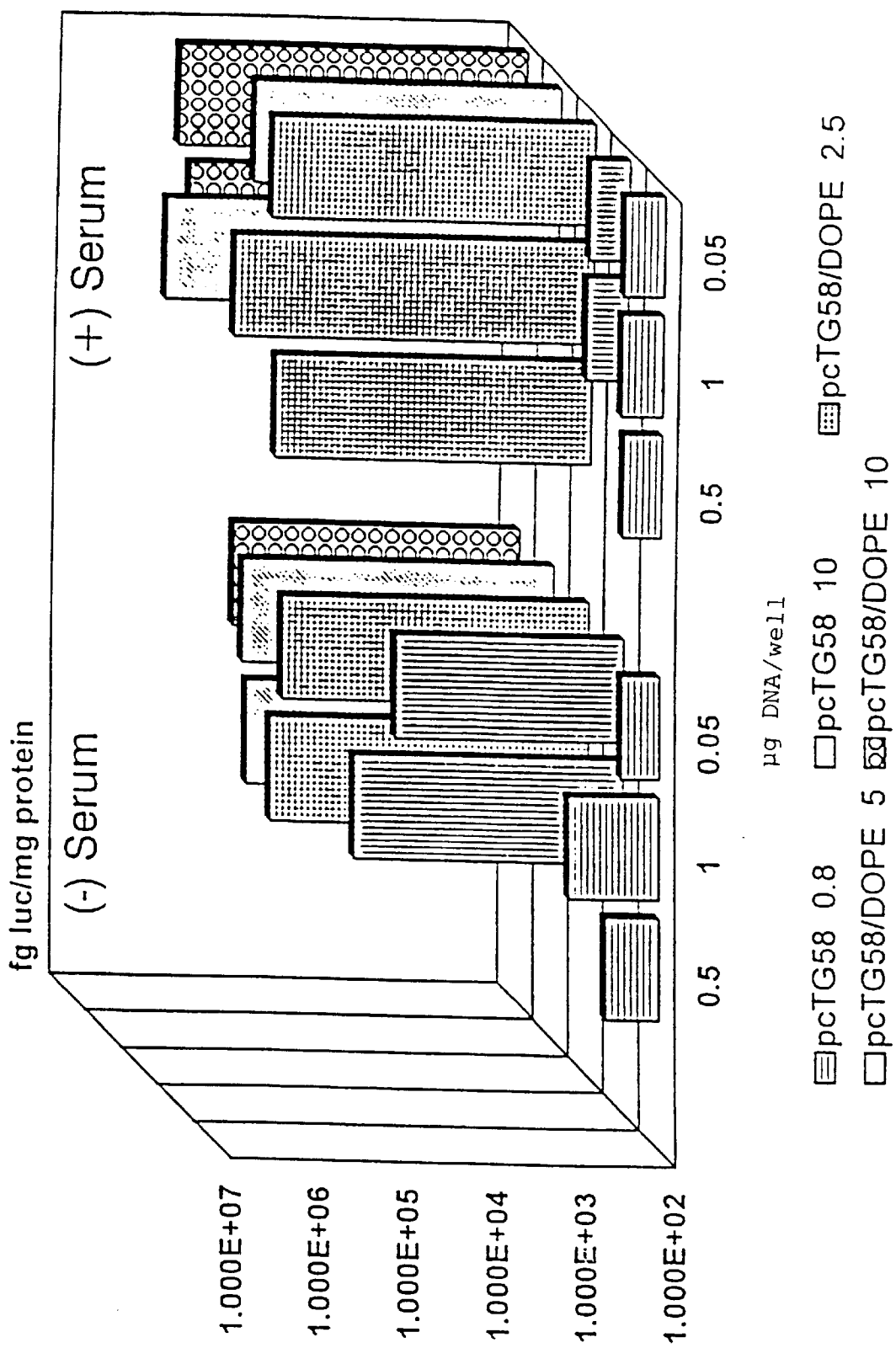
Figure 11:
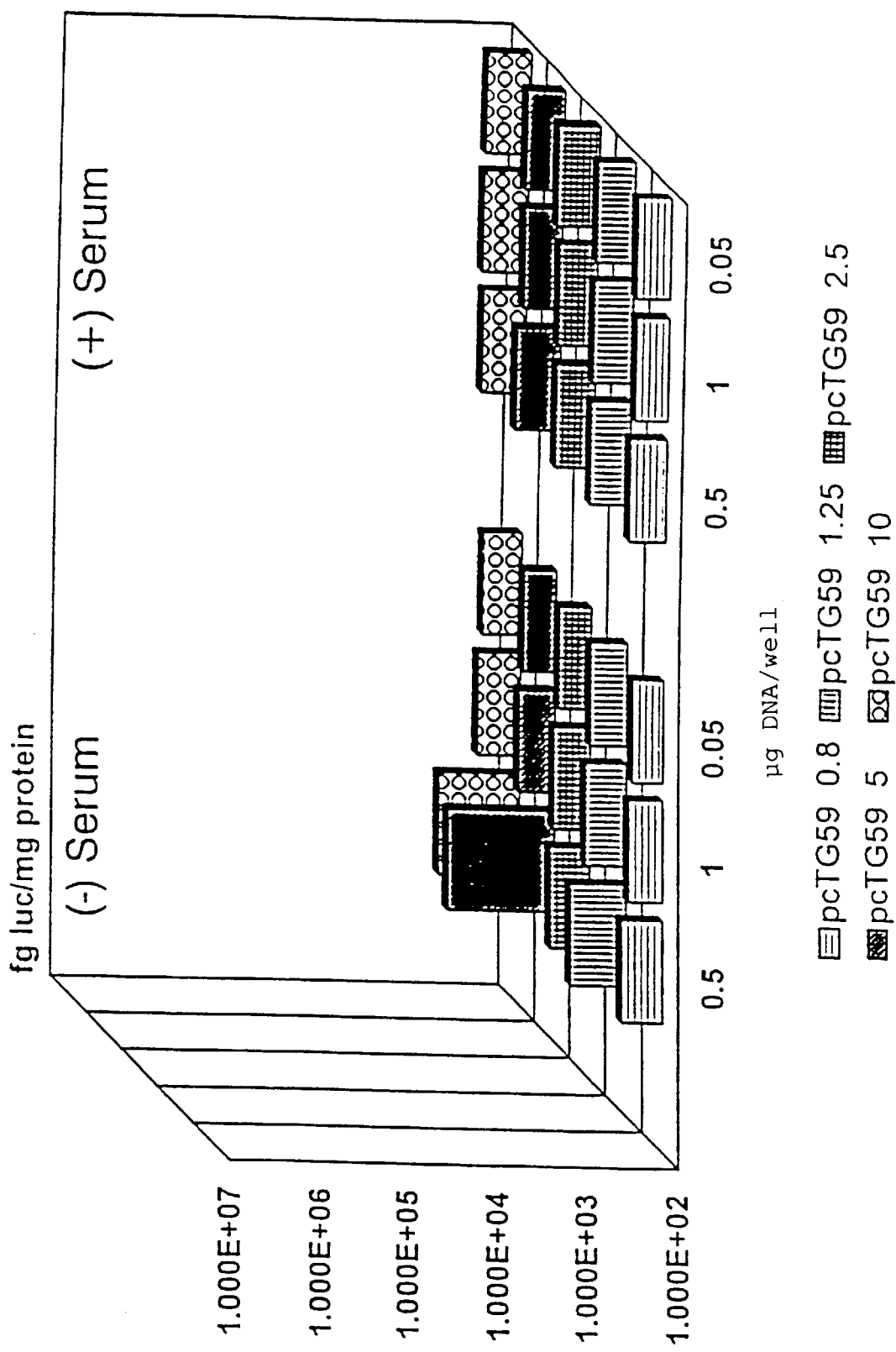
Figure 12:
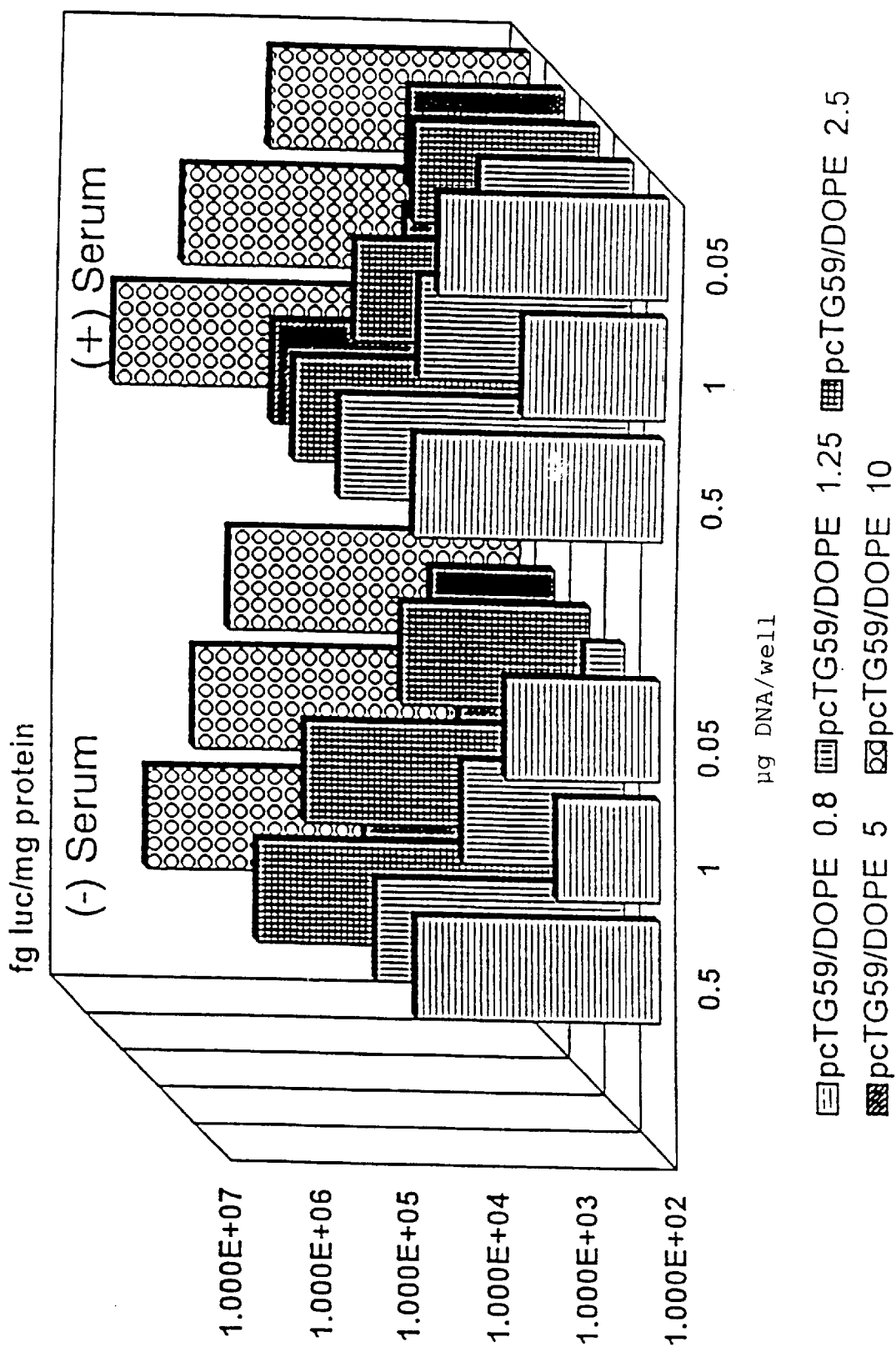
Figure 13:
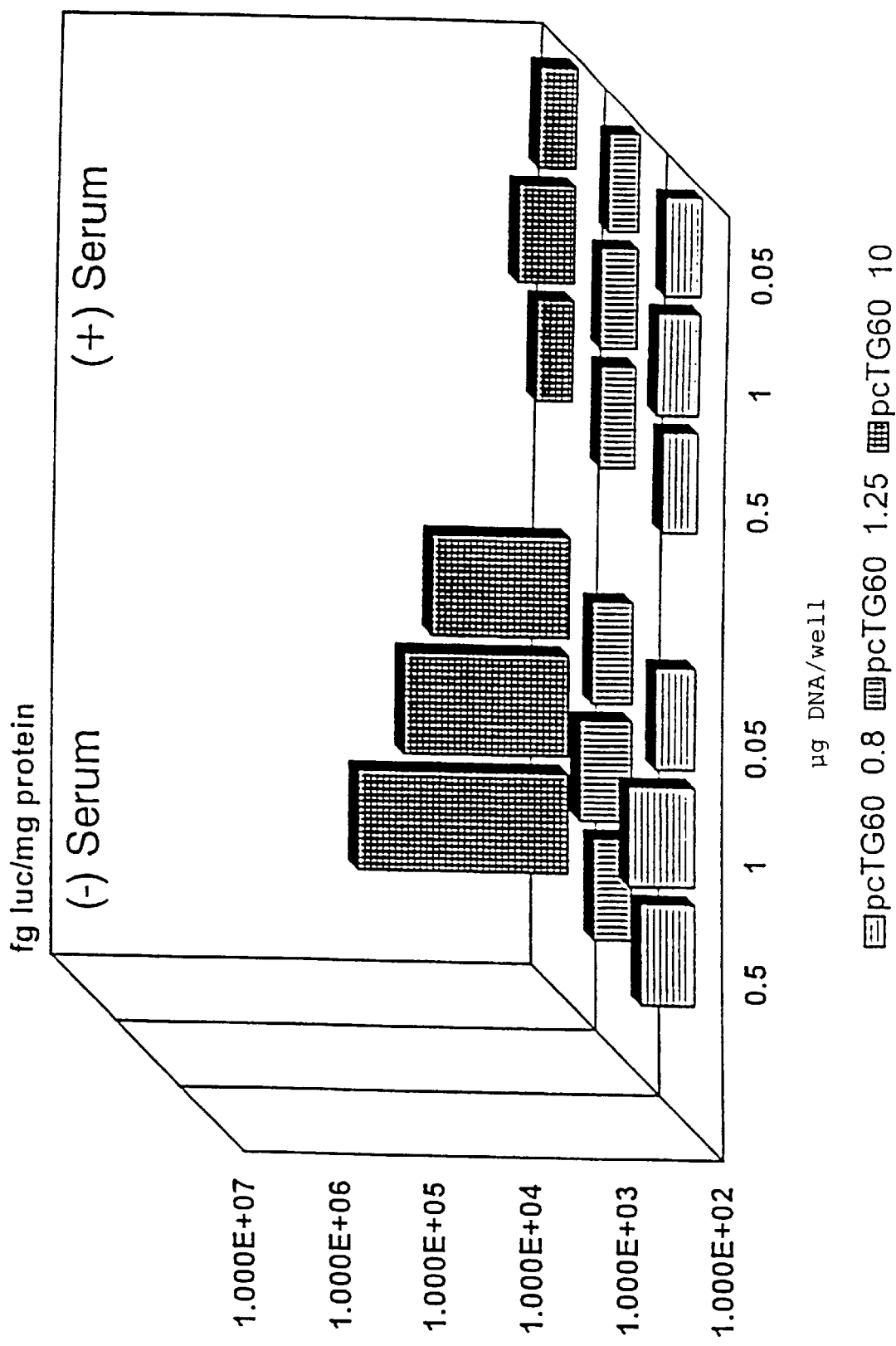
Figure 14:
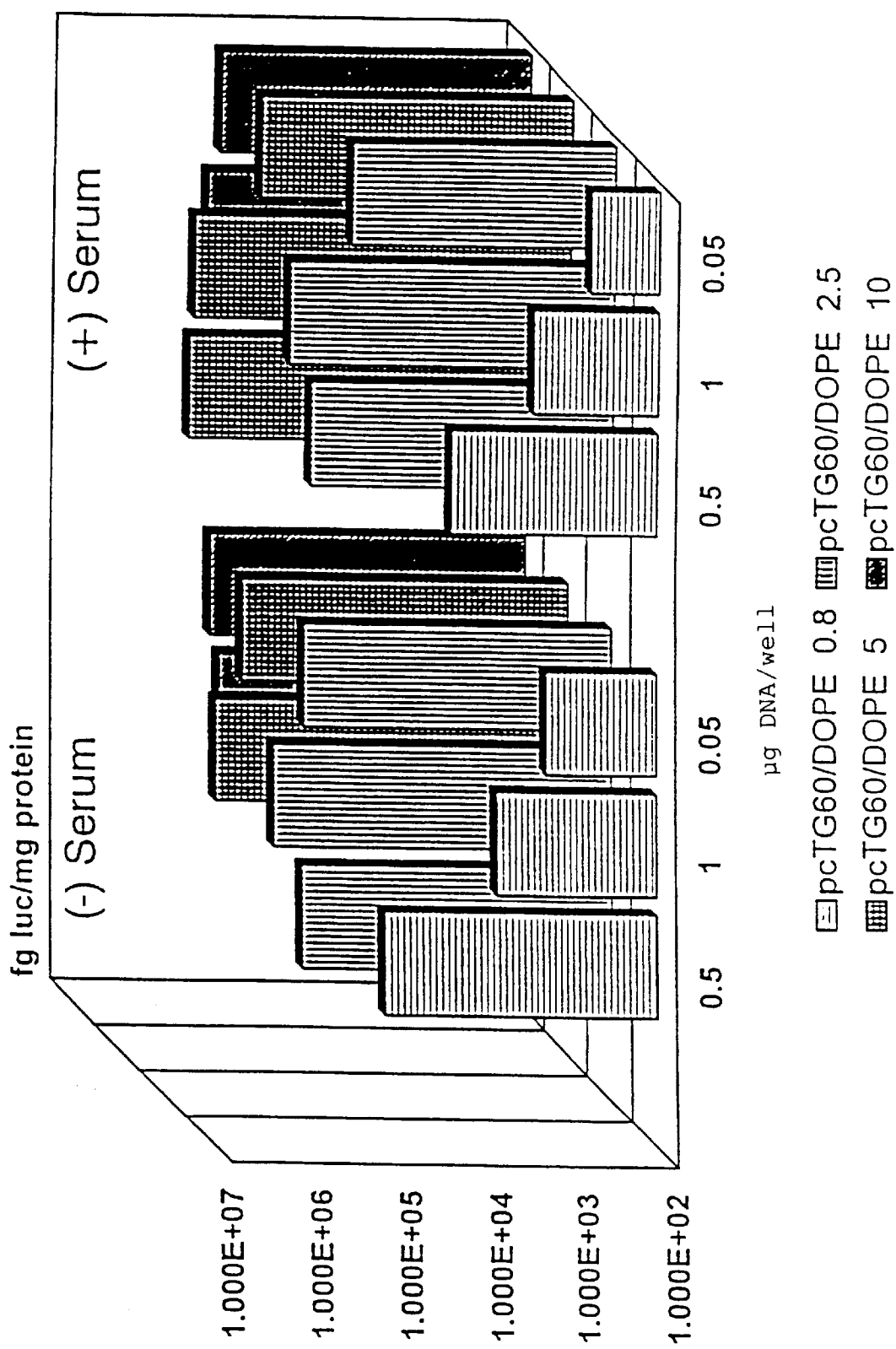

FIGS. 1 to 14 show the results observed after in vitro transfection with complexes containing the lipids (pcTG51 to pcTG54, pcTG57 to pcTG60). The amounts of DNA range from 0.5 to 0.01 μg per well, in the presence or absence of DOPE, for charge ratios ranging from 0.8 to 10 (see figures).

pcTG51 is a diamino cyclic lipid, whose hydrophobic part is 2×$C_{14}$ and no double bonds, containing two positive charges;

pcTG52 is a diaminocyclic lipid, whose hydrophobic part is 2×$C_{14}$ and no double bonds, containing two positive charges;

pcTG53 is a diaminocyclic lipid, whose hydrophobic part is 2×$C_{14}$ and no double bonds, containing two positive charges; this compound contains a hydroxyl group (see description) which makes it more hydrophilic;

pcTG54 is a diaminocyclic lipid, whose hydrophobic part is 2×$C_{16}$ and no double bonds, containing two positive charges;

for the synthesis of pcTG51 to pcTG54, see the above examples;

pcTG57 is a diaminocyclic lipid, whose hydrophobic part is 4×$C_8$ and no double bonds, containing two positive charges;

pcTG58 is a diaminocyclic lipid, whose hydrophobic part is 4×$C_8$ and no double bonds, containing two positive charges;

pcTG57 and pcTG58 are isomers of each other (see description);

pcTG59 is a diaminocyclic lipid, whose hydrophobic part is 4×$C_8$ and no double bonds, containing two positive charges;

pcTG60 is a diaminocyclic lipid, whose hydrophobic part is 4×$C_8$ and no double bonds, containing two positive charges;

pcTG59 and pcTG60 are isomers of each other (see description).

The results observed with the lipids prepared according to the technique described in 1 or 2 are identical.

The conclusions from the results proposed in FIGS. 1 to 14 are:

the complexes containing pcTG51 (FIGS. 1 and 2): the presence of DOPE allows the transfection efficacy to be improved considerably, in particular in the presence of serum. A charge ratio of less than 1.25 is not favorable to transfection.

the complexes containing pcTG52 (FIGS. 3 and 4): the same comment can be made regarding the presence of DOPE. Nevertheless, in the presence of DOPE, and for a 0.8 charge ratio, suitable transfection efficacy is observed here.

the complexes containing pcTG53 (FIGS. 5 and 6): for this lipid, it appears that the choice of the charge ratio is of more decisive importance as regards the efficacy of the transfection obtained. The addition of DOPE allows the inhibiting effect of serum to be corrected.

the complexes containing pcTG54 (FIGS. 7 and 8): the addition of DOPE in the formulation of the corresponding complexes does not appear to play a decisive role when compared with the results observed.

the complexes containing pcTG57 (FIG. 9): the presence of DOPE allows the transfection efficacy to be improved; serum has no influence on this efficacy.

the complexes containing pcTG58 (FIG. 10): DOPE allows the inhibiting effect of serum on the transfection to be corrected.

the complexes containing pcTG59 (FIGS. 11 and 12) or the complexes containing pcTG60 (FIGS. 13 and 14): the presence of DOPE allows the transfection efficacy of the complexes containing such a lipid to be improved considerably, in the presence or absence of serum.

What is claimed is:

1. A complex comprising at least one lipid and at least one active substance, wherein said lipid is pcTG23 having the formula:

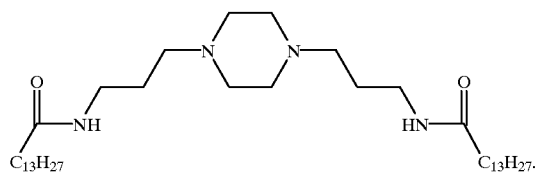

2. The complex according to claim 1 wherein said active substance is selected from the group consisting of nucleic acids and proteins.

3. The complex according to claim 1, wherein the ratio between the number of positive charges in the lipid and the number of negative charges in the active substance is between 0.05 and 20.

4. A preparation comprising at least one complex according to claim 1 and a pharmaceutically acceptable support.

5. The preparation of claim 1, wherein said preparation further comprises at least one adjuvant to stabilize said preparation for the purpose of storage or for enhancing the transfecting power of said complex or both.

6. The complex of claim 1, wherein said complex further comprises a neutral or zwitterionic lipid.

7. The complex of claim 6, wherein said neutral or zwitterionic lipid is phosphatidylethanolamine (PE) or dioleoylphosphatidylethanolamine (DOPE).

* * * * *